(12) United States Patent
Castellano

(10) Patent No.: US 6,302,160 B2
(45) Date of Patent: *Oct. 16, 2001

(54) APPARATUS AND METHOD FOR FILLING AN AMPULE OF A NEEDLE-LESS INJECTOR

(75) Inventor: Thomas P. Castellano, Los Angeles, CA (US)

(73) Assignee: Pen Jet Corporation, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/433,916

(22) Filed: Nov. 3, 1999

Related U.S. Application Data

(63) Continuation-in-part of application No. 09/192,145, filed on Nov. 14, 1998.

(51) Int. Cl.[7] ................................. B65B 1/04; B65B 3/04
(52) U.S. Cl. ................................. 141/9; 141/18; 141/27; 141/100; 141/351; 141/357; 141/363; 141/383; 141/384; 604/82; 604/416
(58) Field of Search ................................. 141/2, 9, 18, 27, 141/100, 311 R, 312, 319–321, 351, 357, 363, 366, 383, 384, 391; 604/48, 56, 68, 82, 416

(56) References Cited

U.S. PATENT DOCUMENTS 4,338,980 * 7/1982 Schwebel et al. ............... 141/18

FOREIGN PATENT DOCUMENTS

| 1258019 | 8/1989 | (CA) | ............... A61M/5/30 |
| 2749169 | 12/1997 | (FR) | ............... A61K/9/08 |
| 9619252 * | 6/1996 | (GB) . | |
| 8908469 | 9/1989 | (WO) | ............... A61M/5/30 |
| 9619252 | 6/1996 | (WO) | ............... A61M/5/30 |
| 9725015 | 7/1997 | (WO) | ............... A61J/1/00 |

* cited by examiner

Primary Examiner—Timothy L. Maust
(74) Attorney, Agent, or Firm—Pillsbury Winthrop LLP

(57) ABSTRACT

An apparatus for filling an ampule of a needle-less injector suitable for injecting liquid medication includes an ampule and a fluid holder. The ampule is for containing the fluid, and the fluid holder is for delivering the fluid. The fluid holder also includes a fluid plunger rod. The ampule is coupled to the fluid holder to provide fluid communication between the ampule and the fluid holder. The fluid plunger rod is depressed to load the fluid from the fluid holder into the ampule to fill the ampule. The ampule may further include an ampule plunger rod. After the ampule is loaded with fluid, the ampule plunger rod is depressed to expel bubbles back into the fluid holder from the ampule.

43 Claims, 25 Drawing Sheets

APPARATUS AND METHOD FOR FILLING AN AMPULE OF A NEEDLE-LESS INJECTOR

RELATED APPLICATIONS

This is a Continuation-In-Part application of U.S. patent application Ser. No. 09/192,145 filed Nov. 14, 1998, which is specifically incorporated by reference herein.

FIELD OF THE INVENTION

This invention relates to devices and methods for filing an ampule of a needle-less injector prior to an injection, and in particular, embodiments for filing an ampule of a needle-less injector or syringe, with a medication prior to administration in an injection.

BACKGROUND OF THE INVENTION

Typically, injections are performed with syringes that pierce the skin with a needle to deliver medication to a desired location on a body. In a large number of cases the syringes are pre-filled with a medication. However, if the medication does not have a long shelf life, it must added to the syringe prior to an injection to maintain potency. This requires the medication to be drawn into the syringe using needles or the like. After drawing in the medication, the injection is administered in a normal manner. But, after the injection there are one or more needles that need to be disposed of, increasing costs and increasing the potential health hazards from exposure to used needles.

As an alternative to needle delivery injections, needle-less medication injections have been performed with "permanent gun" instruments, generally referred to as "jet injectors". These devices use either a compression spring or a compressed inert gas to propel the fluid medication (via a push rod plunger) through a small orifice (an injector nozzle) which rests perpendicular to and against the injection site. The fluid medication is generally accelerated at a high rate to a speed of between about 800 feet per second (fps) and 1,200 fps (approximately 244 and 366 meters per second, respectively). This causes the fluid to pierce through the skin surface without the use of a needle, resulting in the medication being deposited in a flower pattern under the skin surface. These reusable jet injectors can accept pre-loaded medication cartridges, but again the cartridges must be pre-loaded just prior to an injection for certain medications with short shelf lives. The procedure is to again use a needle and a syringe to load the medication in the cartridge prior to an injection. After drawing in the medication, the needle-less injection is administered in a normal manner. But, after the injection there are again one or more needles that need to be disposed of, increasing costs and increasing the potential health hazards from exposure to used needles.

Single use needle-less jet injectors offer an alternative to multi-use, needle-less injectors, since they are low cost and can be pre-loaded at the point of manufacture. However, if the medication does not have a long shelf life, the pre-loading is impractical. Thus, single-use, needle-less injectors have not been usable with medications that must be loaded prior to injection.

SUMMARY OF THE DISCLOSURE

It is an object of an embodiment of the present invention to provide an improved device and method for filing an ampule of a needle-less injector, syringe or the like, that obviates for practical purposes, the above-mentioned limitations.

According to an embodiment of the present invention, an apparatus for filling an ampule of a needle-less injector suitable for injecting fluid includes an ampule and a fluid holder. The ampule is for containing the fluid, and the fluid holder is for loading the fluid. The fluid holder also includes a fluid plunger rod. In preferred embodiments, the ampule is coupled to the fluid holder to provide fluid communication between the ampule and the fluid holder. Also, the fluid plunger rod is depressed to load the fluid from the fluid holder into the ampule to fill the ampule of the needle-less injector. In further embodiments, the ampule further includes an ampule plunger rod. After the ampule is loaded with the fluid, the ampule plunger rod is depressed to expel bubbles back into the fluid holder from the ampule of the needle-less injector. Preferably, the ampule is loaded with fluid just prior to injection of the fluid due to a short shelf life of the fluid. Also, the ampule of the needle-less injector is attached to the needle-less injector after filing with the fluid.

According to further embodiments of the present invention, a method of filling an ampule of a needle-less injector suitable for injecting fluid includes the steps of: providing an ampule for containing the fluid; providing a fluid holder containing a fluid; providing the fluid holder with a fluid plunger rod; coupling the ampule to the fluid holder to provide fluid communication between the ampule and the fluid holder; and depressing the fluid plunger rod to load the fluid into the ampule to fill the ampule of the needle-less injector. Further embodiments include the steps of: providing the ampule with an ampule plunger rod; and depressing the ampule plunger rod, after the ampule is loaded with fluid, to expel bubbles back into the fluid holder from the ampule of the needle-lee injector. Preferably, the step of filling the ampule occurs just prior to injection of the fluid due to a short shelf life of the fluid. Also, the method includes the step of attaching the ampule of the needle-less injector to the needle-less injector after filing with the liquid medication.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 1:
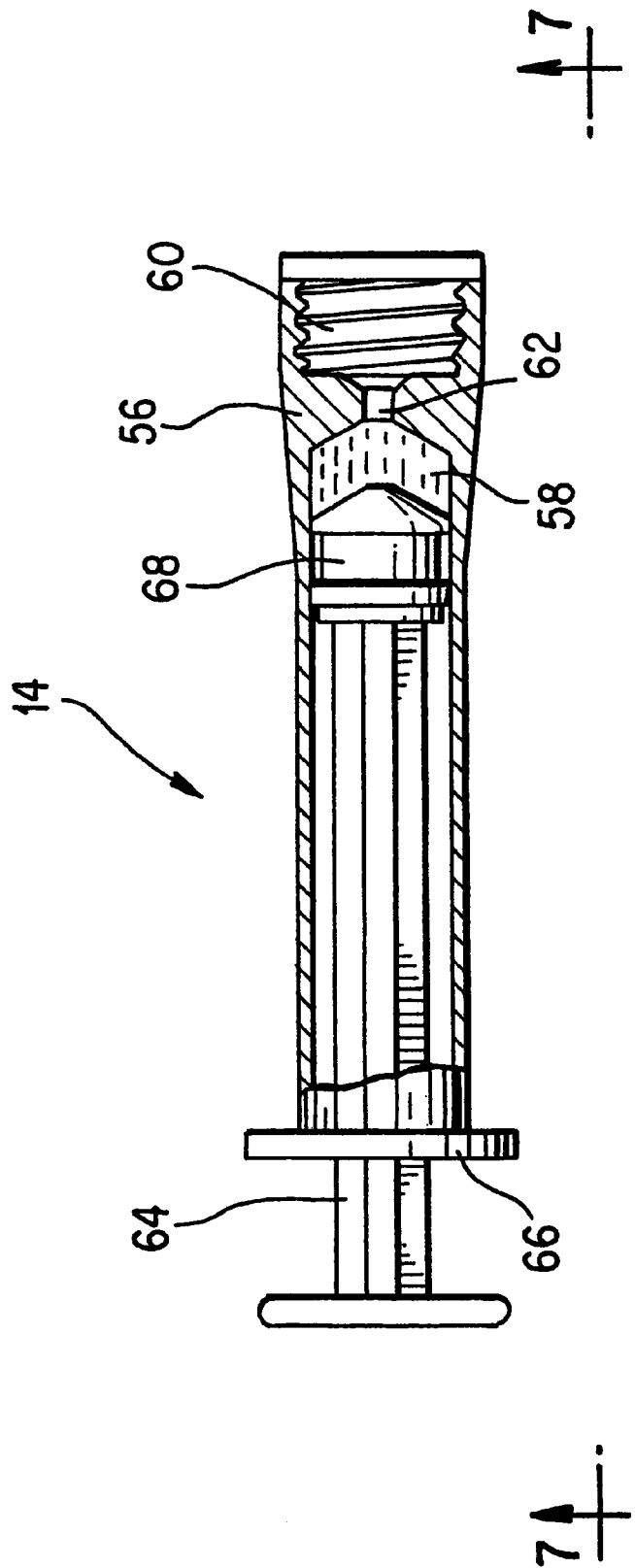
FIG. 1 is a side plan view of a transparent reagent holder in accordance with an embodiment of the present invention.
Figure 3:
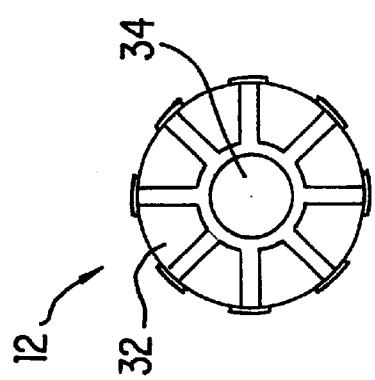
FIG. 3 is an end plan view of the ampule shown in FIG. 2.
Figure 2:
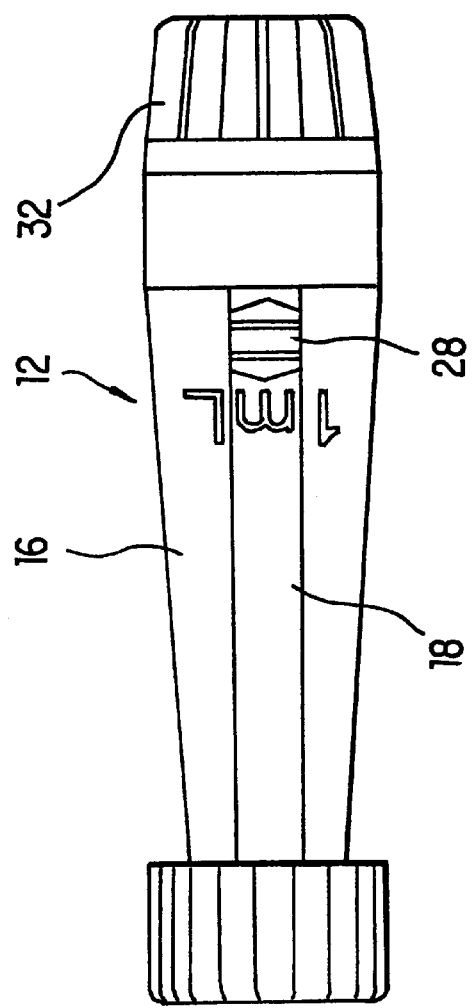
FIG. 2 is a side plan view of an ampule for a needle-less injector in accordance with an embodiment of the present invention.
Figure 4A:
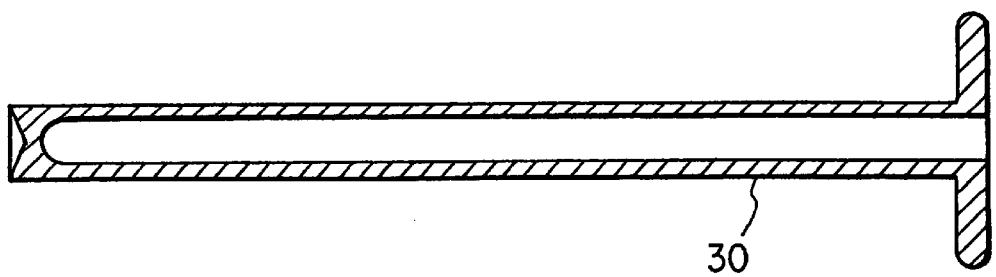
FIG. 4A is a cross-sectional view of a diluent plunger rod in accordance with an embodiment of the present invention.
Figure 4B:
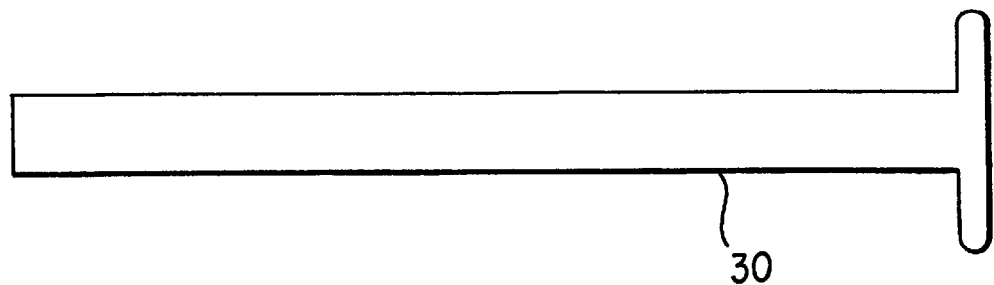
FIG. 4B is a side plan view of a diluent plunger rod in accordance with an embodiment of the present invention.

As shown in the drawings for purposes of illustration, the invention is embodied in a device and method for filing an ampule of a single-use needle-less injector with medication prior to administration of an injection. Preferably, the device is used in conjunction with, or are attached to, a single-use disposable needle-less injector, such as that disclosed in U.S. Pat. application Ser. No. 08/719,459 filed Sep. 25, 1996, and Ser. No. 08/727,911 filed Oct. 9, 1996, which are herein incorporated by reference. However, it will be recognized that further embodiments of the invention may be used to fill an ampule in multiple-use needle-less injectors, conventional syringes, infusion injections and the like.

FIGS. 1–11 illustrate a filling apparatus 10 in accordance with an embodiment of the present invention. The filling apparatus 10 includes a diluent holder 12 and a regent holder 14.

The diluent holder 12 is sized to contain a diluent for producing a medication prior to injection. In preferred embodiments, the diluent holder 12 is an ampule for use on a needle-less injector 1000 (see FIG. 11). However, in alternative embodiments, the diluent holder 12 may be another receptacle for loading diluent into another container, such as an ampule for a multiple-use needle-less injector, syringe or the like. The diluent holder 12 includes a housing 16 that forms an interior chamber 18 for holding the diluent. In preferred embodiments, the diluent is sterile water, saline, buffered solution or other solvent that is mixed with a reagent to form a liquid medication. One end of the housing 16 includes threads 20 and an orifice 22 for mating with corresponding threads and opening on the reagent holder 14 to provide fluid communication between the diluent holder 12 and the reagent holder 14. Another end of the housing 16 includes threads 24 and an opening 26 for mating with corresponding needle-less injector 1000. In alternative embodiments, the ends of the diluent holder 12 may be formed with other attachment structures, such as snaps, bars, friction fits or the like.

Figure 5:
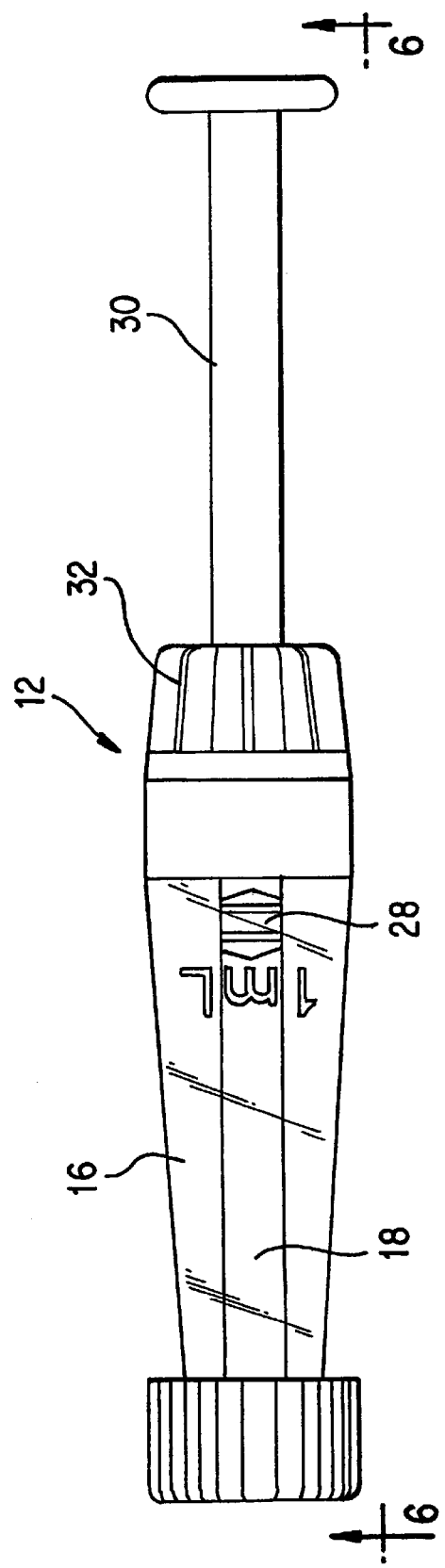
FIG. 5 is a side plan view of the ampule of FIGS. 2 and 3 combined with the plunger rod shown in FIG. 4.
Figure 6:
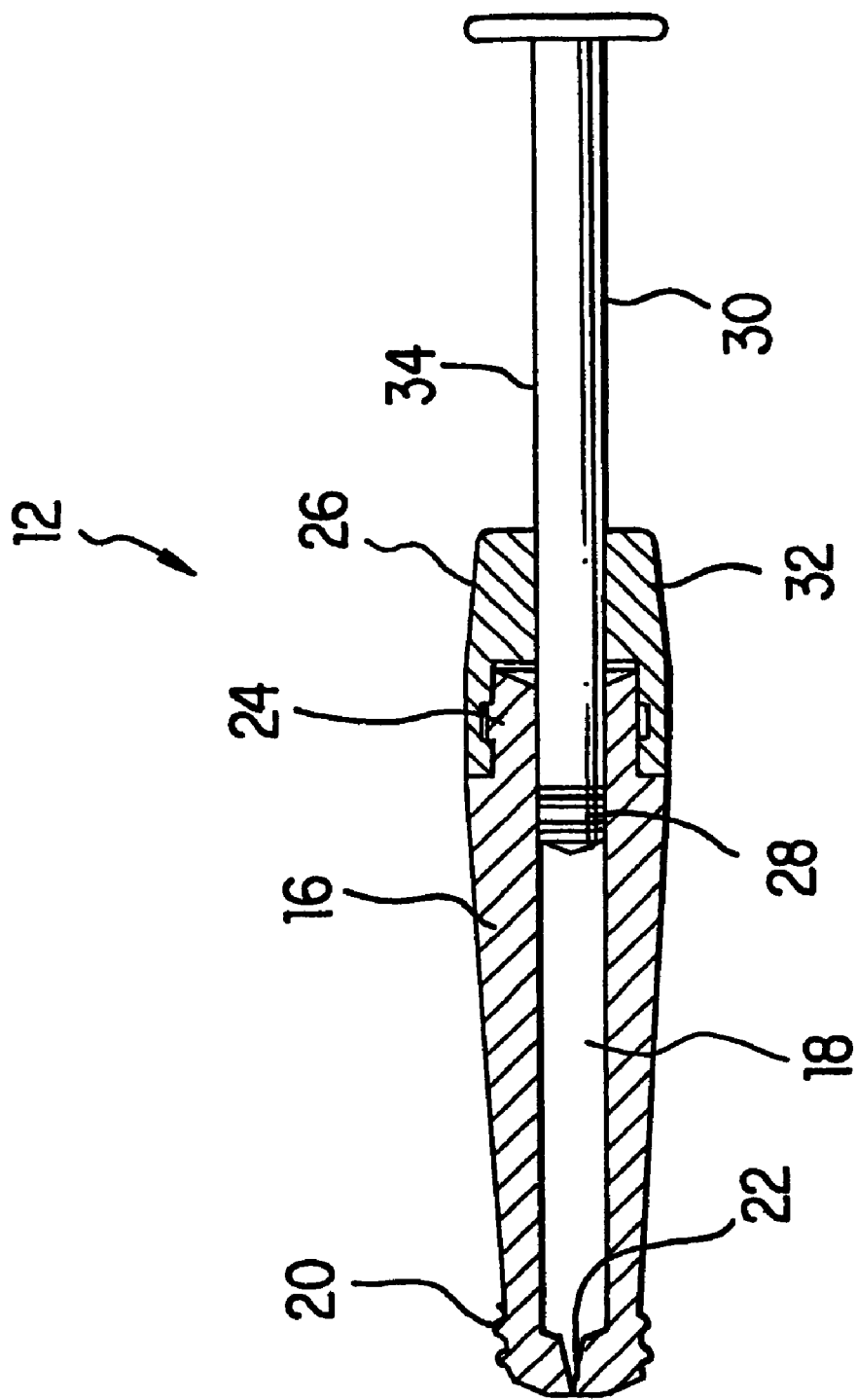
FIG. 6 is a cross-sectional view of the ampule and plunger rod as shown along the line 6—6 in FIG. 5.
Figure 7:
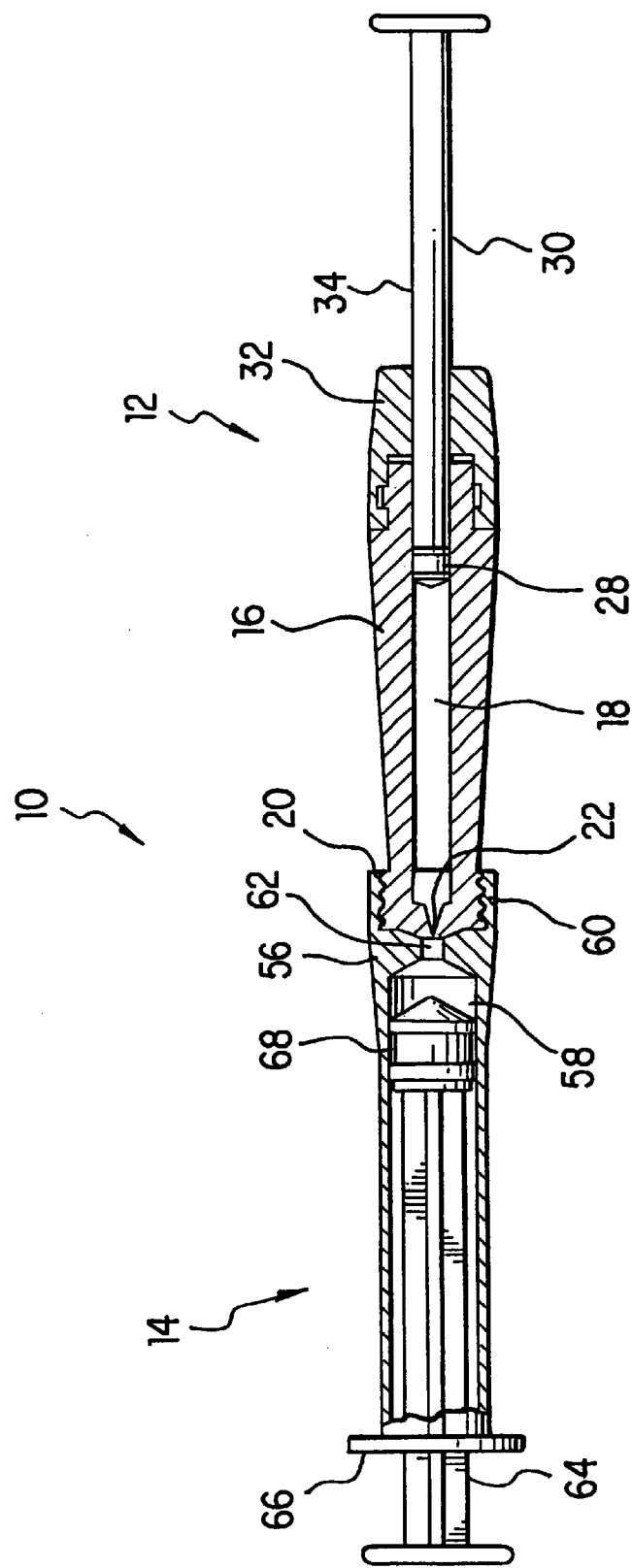
FIG. 7 is a cross-sectional view of the reagent holder, as shown along line 7—7 in FIG. 1 coupled to the ampule and plunger rod as shown in FIG. 6, prior to mixing the reagent and the diluent in the reagent holder.
Figure 8:
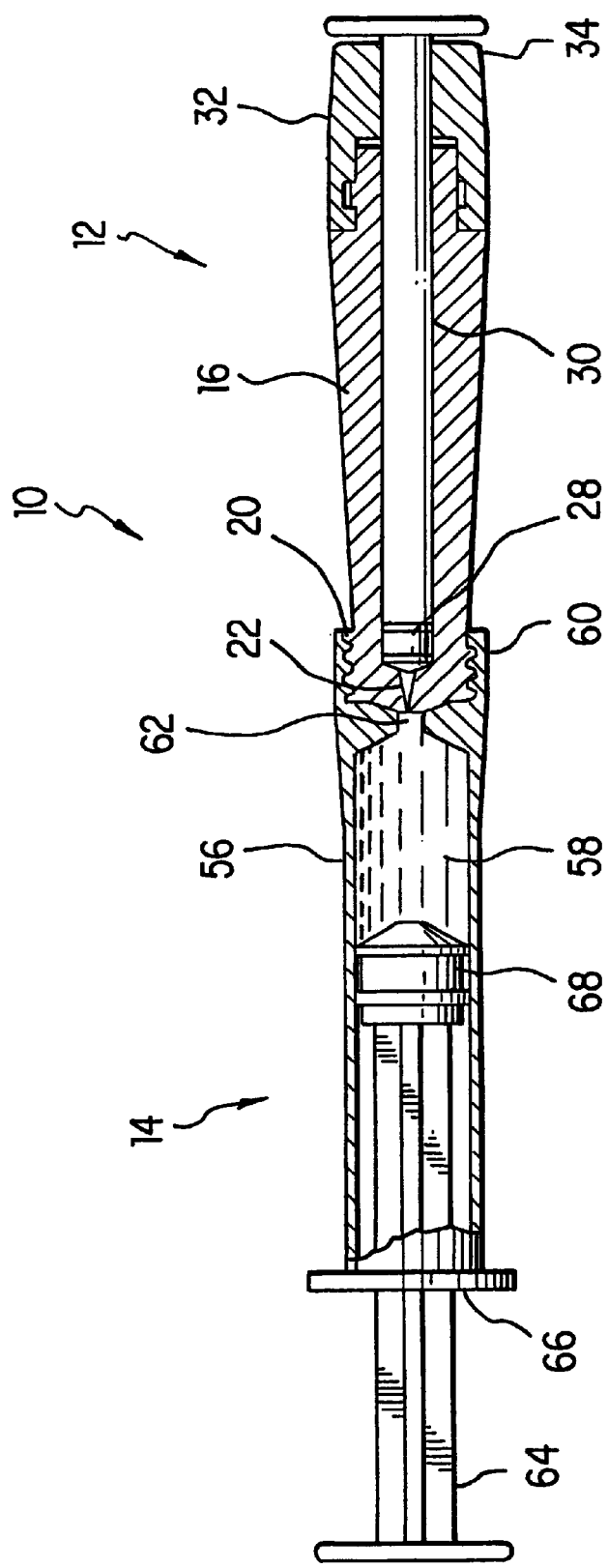
FIG. 8 is a cross-sectional view of the reagent holder and ampule, shown in FIG. 7, after the diluent plunger rod has been depressed to load the diluent into the reagent for mixing.
Figure 9:
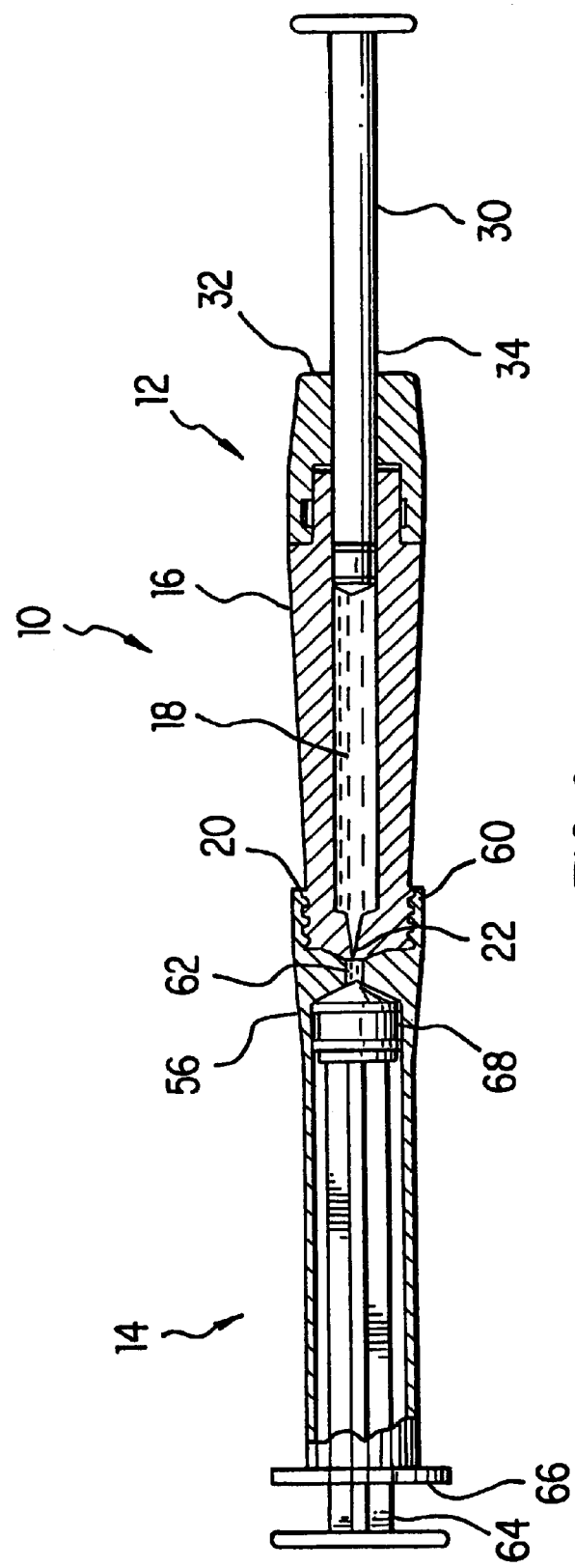
FIG. 9 is a cross-sectional view of the reagent holder and ampule, shown in FIG. 8, after the medication has been mixed and the reagent plunger rod is depressed to reload the mixed reagent and diluent in the ampule for an injection.
Figure 10:
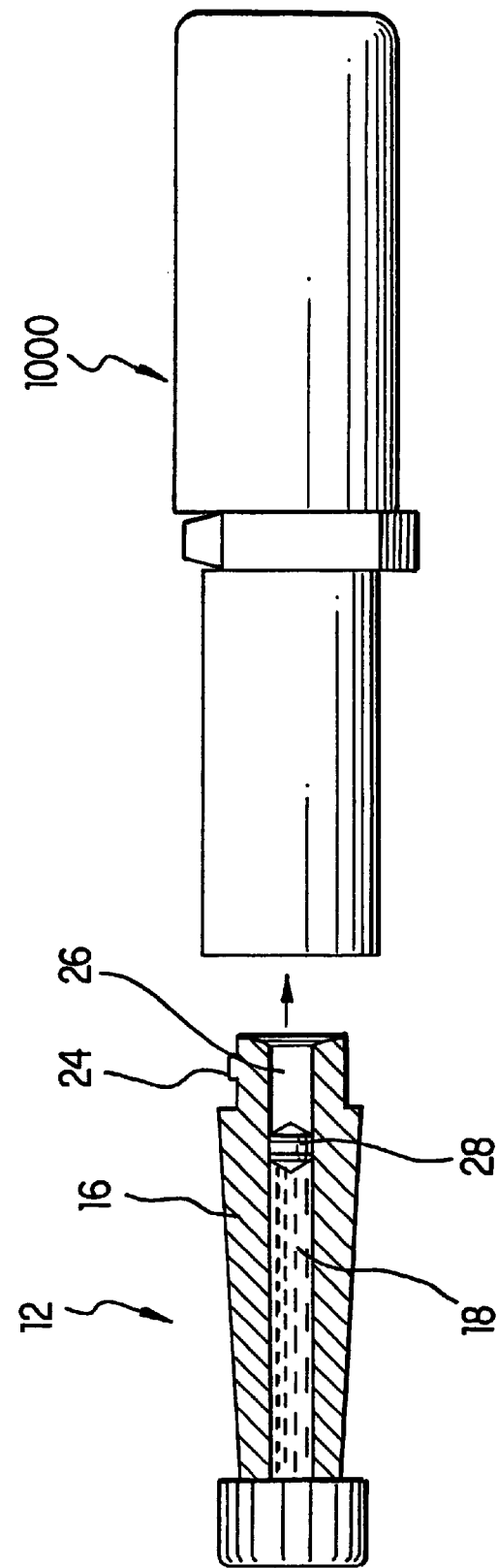
FIG. 10 is a partial cross-sectional view and side plan view of an ampule that is to be mated to a needle-less injector in accordance with an embodiment of the present invention.
Figure 11:
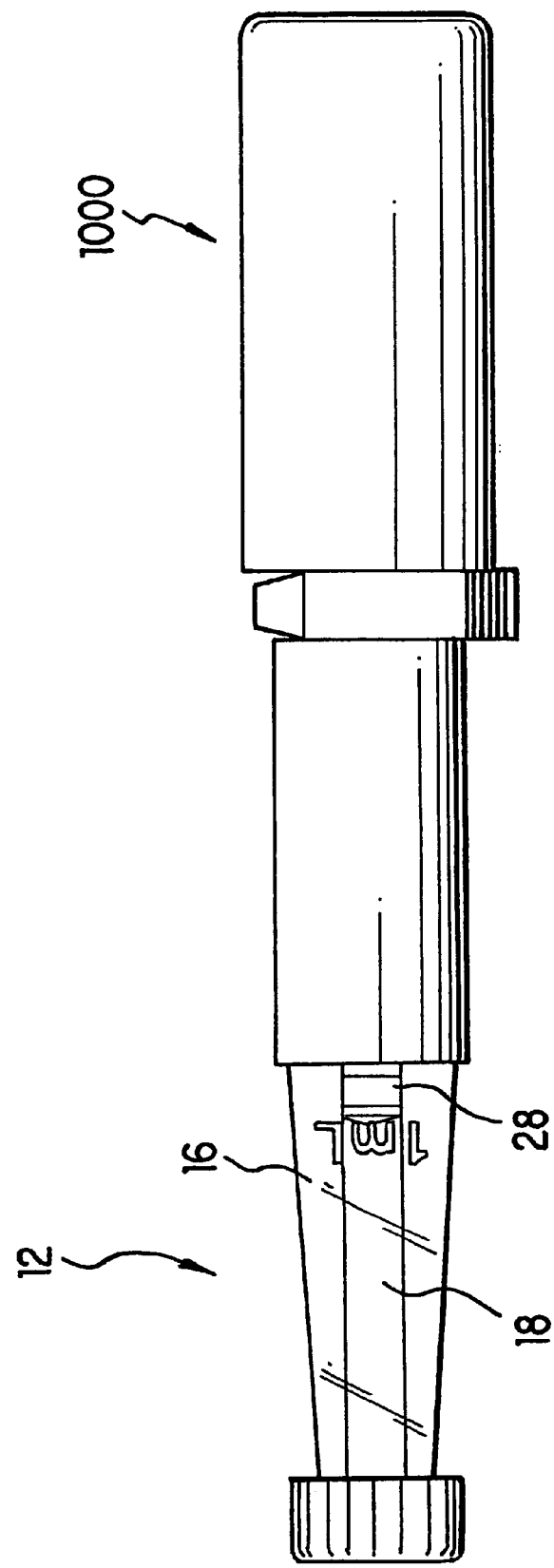
FIG. 11 is a side plan view of the assembled needle-less injector prior to administering an injection in accordance with an embodiment of the present invention.
Figure 12:
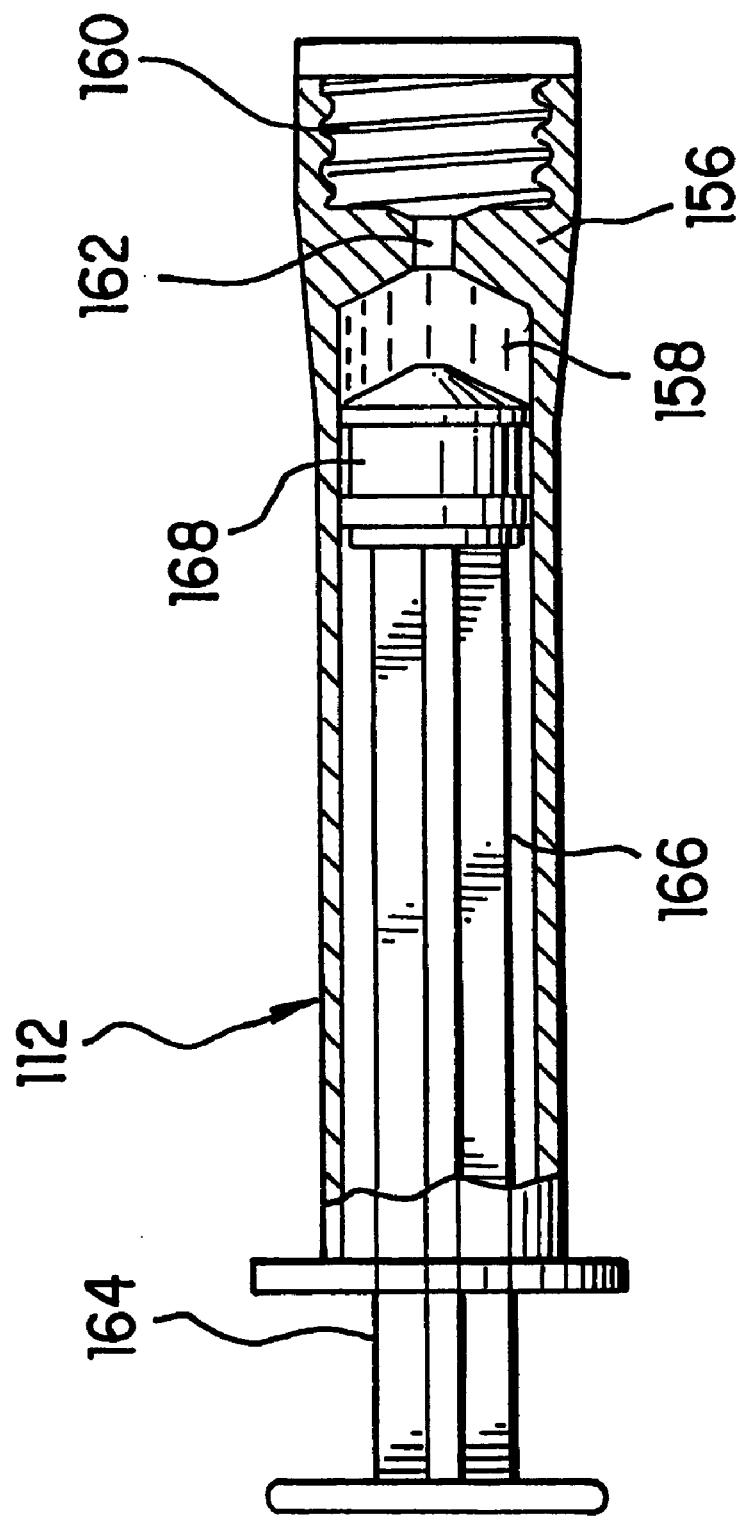
FIG. 12 is a side plan view of a transparent diluent holder in accordance with another embodiment of the present invention.
Figure 13:
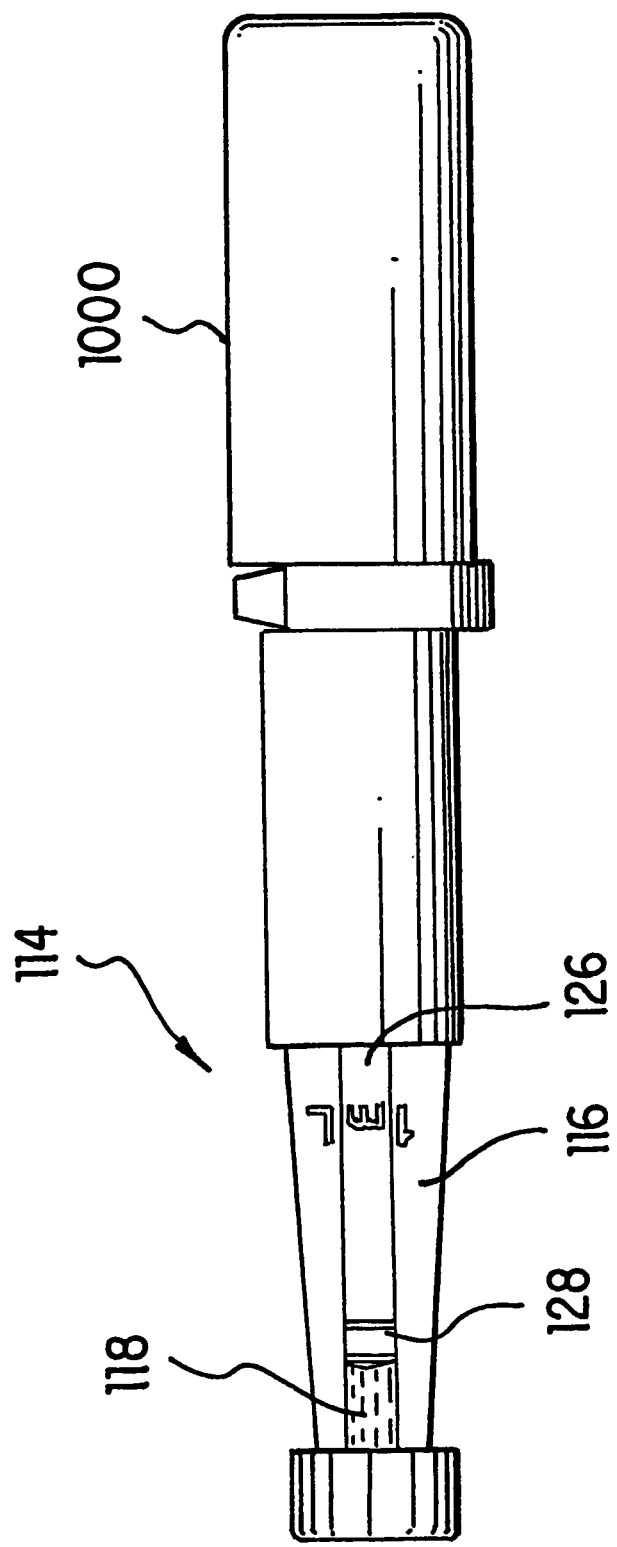
FIG. 13 is a side plan view of an ampule and a needle-less injector in accordance with another embodiment of the present invention.
Figure 14:
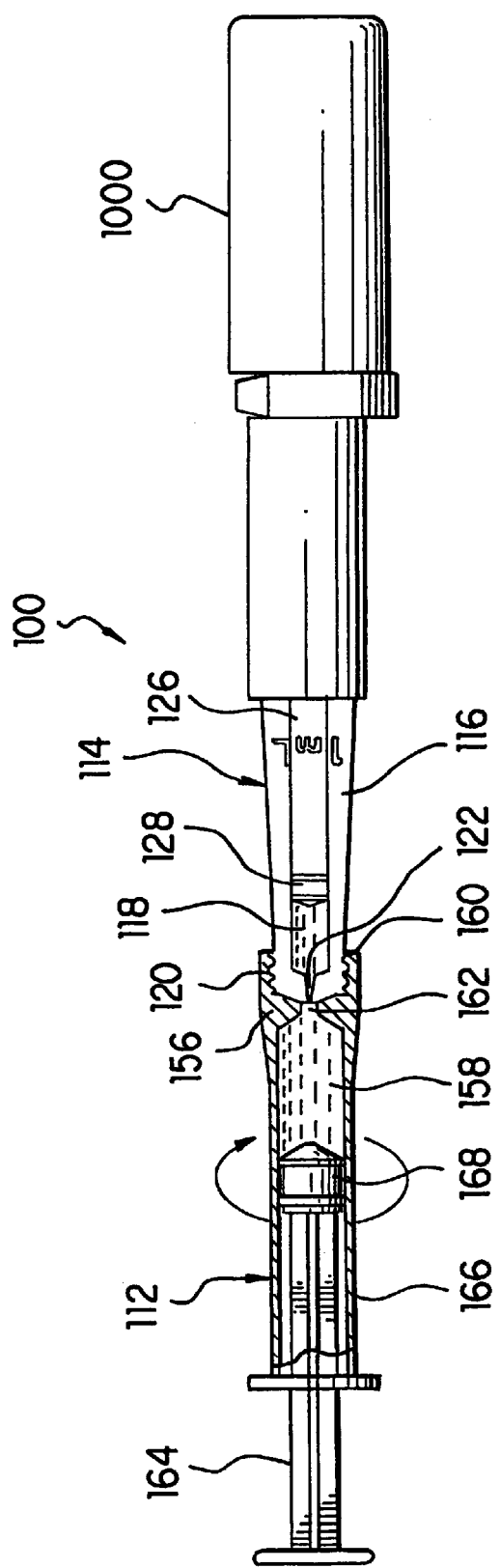
FIG. 14 is a cross-sectional view of the diluent holder coupled to the ampule reagent holder and the needle-less injector prior to mixing the reagent and the diluent in the reagent holder.
Figure 15:
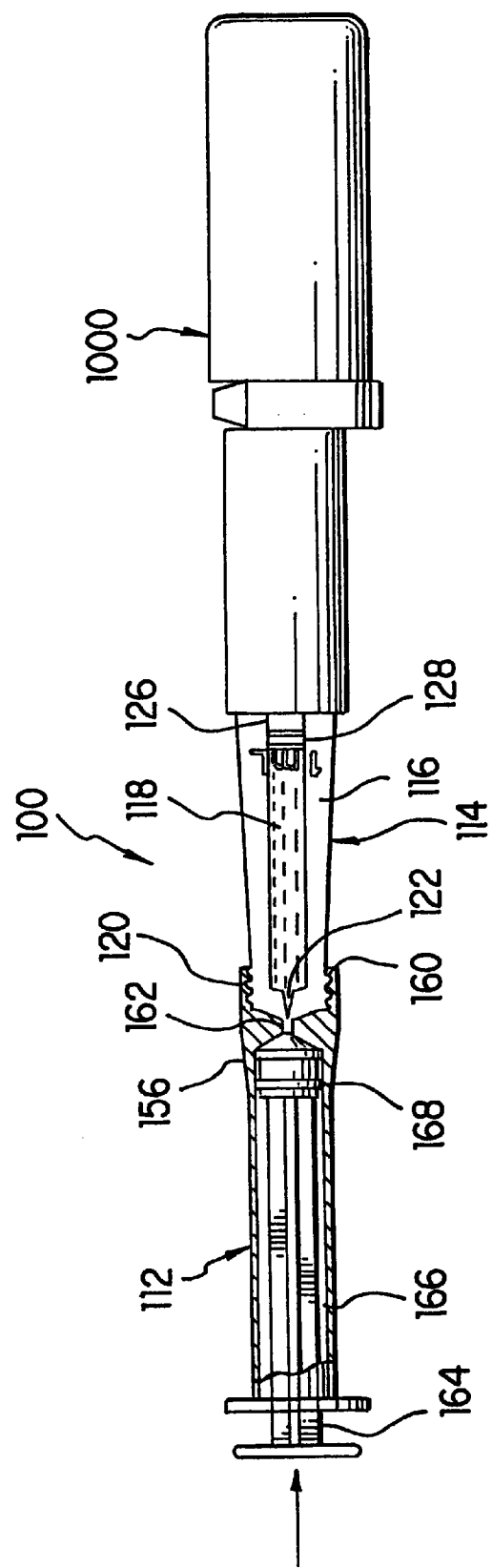
FIG. 15 is a cross-sectional view of the diluent holder coupled to the ampule reagent holder and the needle-less injector after the diluent plunger rod has been depressed to load the diluent into the reagent for mixing.

The diluent holder 12 also includes a piston 28 for maintaining the diluent in the interior chamber 18 and substantially prevent leakage out of the opening 26 of the housing 16. The piston 28 maintains the diluent in the interior chamber 18 so that it does not leak out of the orifice 22. As shown in FIGS. 5–6, the diluent holder includes a diluent plunger 30 and a support bushing 32 having an opening 34 that allows passage of the diluent plunger rod 32 through the support bushing 32 to expel diluent.

The reagent holder 14 is sized to contain a reagent for producing a medication prior to injection when mixed with the diluent of the diluent holder 12. The reagent holder 14 includes a housing 56 that forms an interior chamber 58 for holding the reagent. In preferred embodiments, the reagent is or other reagent needed to produce a liquid medication. One end of the housing 56 includes threads 60 and an opening 62 for mating with corresponding threads 20 and orifice 22 on the diluent holder 12 to provide fluid communication between the diluent holder 12 and the reagent holder 14. In alternative embodiments, the end of the reagent holder 14 may be formed with other attachment structures, such as snaps, bars, friction fits or the like. Another end of the housing 56 includes a reagent plunger 64 and an opening 66 for receiving the reagent plunger 64.

The reagent holder 14 also includes a piston 68 coupled to the end of the reagent plunger 64 for maintaining the reagent in the interior chamber 58 and to substantially prevent leakage out of the opening 66 of the housing 56. The piston 68 maintains the reagent in the interior chamber 58 so that it does not leak out of the opening 62.

As shown in FIGS. 1–11, the reagent holder 14 stores the reagent and is configured for sterile docking (or coupling) with the diluent holder 12 containing the diluent. When the diluent holder 12 is docked with the reagent holder 14, the diluent plunger 30 is pushed through the bushing 32 on the diluent holder 12 to transfer and load the diluent into the reagent holder 14, by moving the diluent plunger 30 and piston 28 towards the orifice 22. As the diluent enters the reagent holder 14, the diluent and reagent are mixed together to produce the medication. Once the medication is produced, the reagent plunger 64 and piston 68 are moved towards the opening 62 in the housing 56 of the reagent holder 14 to reload the mixed medication back into the diluent holder 12. In preferred embodiments, diluent holder 12 is the ampule for a needle-less injector or the like. After reloading the diluent holder 12, the diluent plunger 30 and the bushing 32 are removed and discarded from the diluent holder 12. The diluent holder, if an ampule, is then threaded onto the body of a needle-less injector 1000. Once seated, the reagent holder 14 is removed from the end of diluent holder 12, and final tightening is performed on the diluent holder 12. A needle-less injection is then performed in a normal manner.

In alternative embodiments, if the diluent holder 12 is not an ampule for a needle-less injector, the reagent holder 14, may be removed after receiving the diluent, and then coupled to an ampule for filling with the mixed medication. In further embodiments, the diluent holder 12 may be an ampule for a multi-use needle-less injector, syringe or the like.

FIGS. 12–18 illustrate a filling apparatus 100 in accordance with an embodiment of the present invention. The filling apparatus 100 includes a diluent holder 112 and a regent holder 114. The filling apparatus 100 is similar to the apparatus 10 described above; however, the filing apparatus 100 contains the reagent in the ampule for a needle-less injector, syringe or the like. This removes one step of reloading the ampule after mixing the reagent and diluent to produce the medication.

The reagent holder 114 is sized to contain a regent for producing a medication prior to injection. In preferred embodiments, the reagent holder 114 is an ampule for use on a needle-less injector 1000 (see FIG. 11). The reagent holder 114 includes a housing 116 that forms an interior chamber 118 for holding the reagent. In preferred embodiments, the reagent is that is mixed with a diluent to form a liquid medication. One end of the housing 116 includes threads 120 and an orifice 122 for mating with corresponding threads and opening on the diluent holder 112 to provide fluid communication between the diluent holder 112 and the reagent holder 114. Another end of the housing 116 includes threads (not shown) and an opening 126 for mating with corresponding needle-less injector 1000. In alternative embodiments, the ends of the reagent holder 114 may be formed with other attachment structures, such as snaps, bars, friction fits or the like.

The reagent holder 114 also includes a piston 128 for maintaining the reagent in the interior chamber 118 and substantially prevent leakage out of the opening 126 of the housing 116. The piston 128 maintains the reagent in the interior chamber 118 so that it does not leak out of the orifice 122. As shown in FIGS. 13–18, the reagent holder 114 is attached to the needle-less injector 1000. In alternative embodiments, the reagent holder 14 is filled separately from the needle-less injector 1000 and includes a reagent plunger and a support bushing having an opening that allows passage of the reagent plunger rod through the support bushing to adjust the piston 128 after receipt of the diluent, in a manner and structure similar to that described in the first embodiment above.

The diluent holder 112 is sized to contain a diluent for producing a medication prior to injection when mixed with the reagent of the reagent holder 114. The diluent holder 112 includes a housing 156 that forms an interior chamber 158 for holding the diluent. In preferred embodiments, the diluent is sterile water, saline, buffered solution or other solvent that is mixed with a reagent to form a liquid medication. One end of the housing 156 includes threads 160 and an opening 162 for mating with corresponding threads 120 and orifice 122 on the reagent holder 114 to provide fluid communication between the diluent holder 112 and the reagent holder 114. In alternative embodiments, the end of the diluent holder 112 may be formed with other attachment structures, such as snaps, bars, friction fits or the like. Another end of the housing 156 includes a diluent plunger 164 and an opening 166 for receiving the diluent plunger 64.

The diluent holder 112 also includes a piston 168 coupled to the end of the diluent plunger 164 for maintaining the diluent in the interior chamber 158 and to substantially prevent leakage out of the opening 166 of the housing 156. The piston 168 maintains the diluent in the interior chamber 158 so that it does not leak out of the opening 162.

Figure 16:
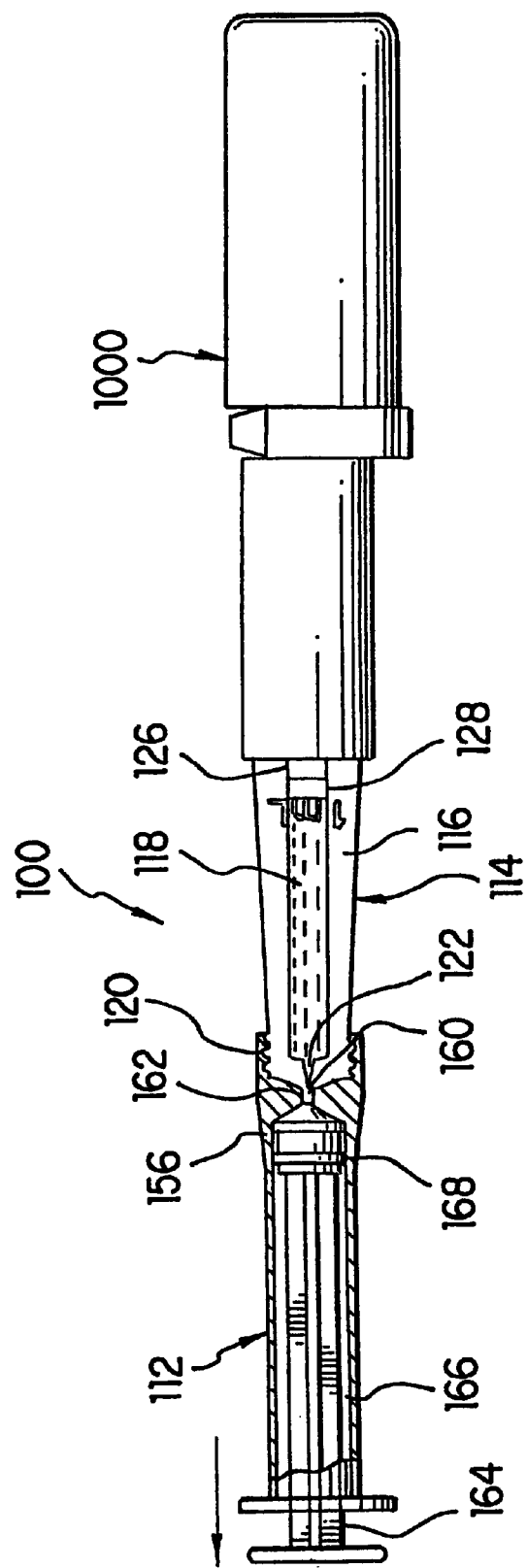
FIG. 16 is a cross-sectional view of the diluent holder coupled to the ampule reagent holder and the needle-less injector after the medication has been mixed and the diluent plunger rod is withdrawn to remove air from the mixed reagent and diluent in the ampule reagent holder.
Figure 17:
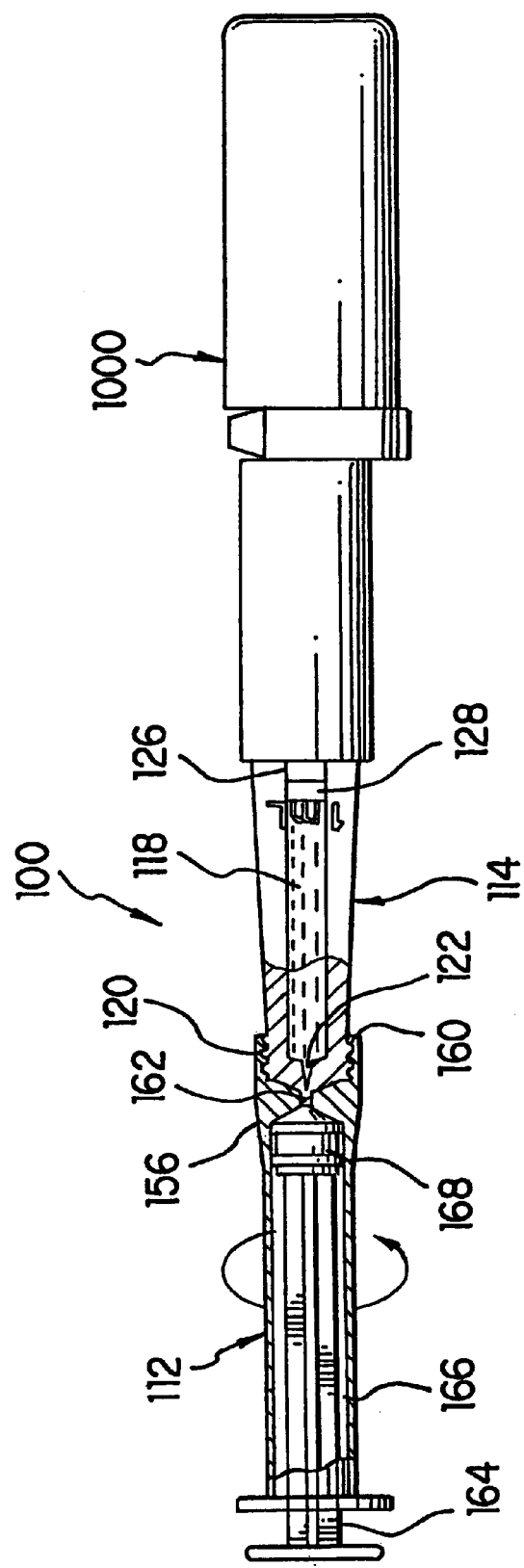
FIG. 17 is a cross-sectional view of an a diluent holder coupled to the ampule reagent holder and needle-less injector prior to removal to permit an injection.
Figure 18:
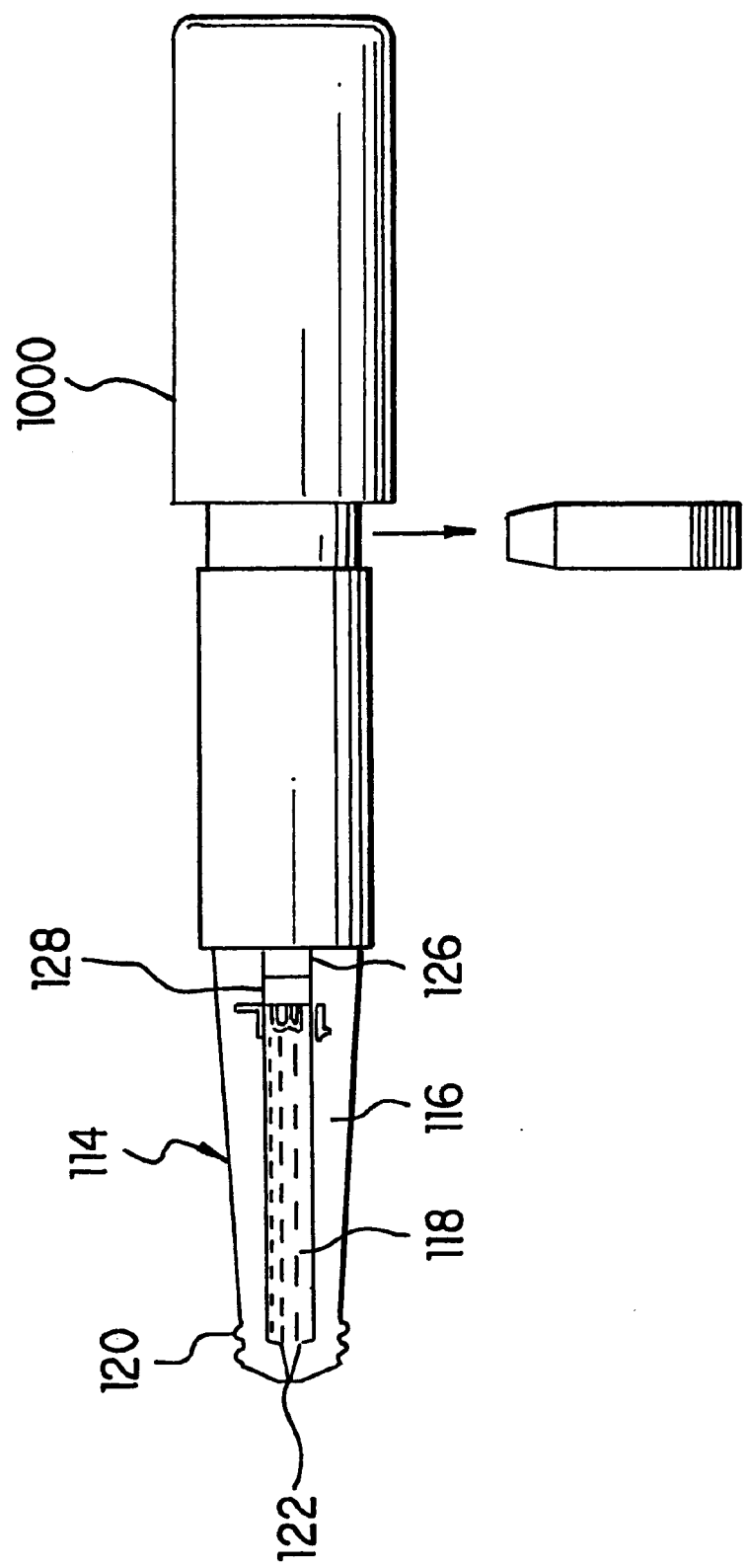
FIG. 18 is a partial cross-sectional and side plan view of the assembled needle-less injector prior to administering an injection in accordance with another embodiment of the present invention.
Figure 19:
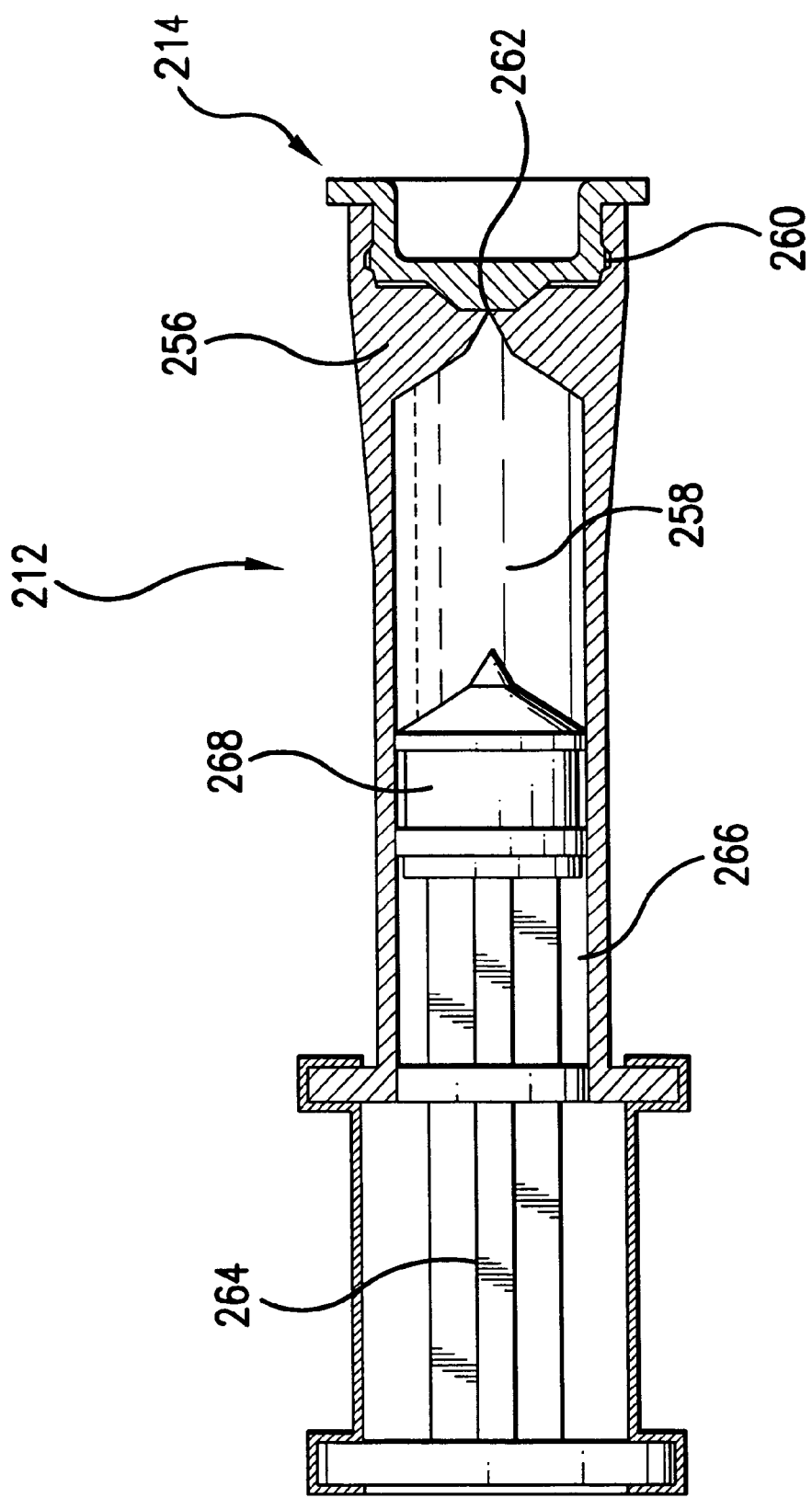
FIG. 19 is a cross-sectional plan view of a transparent fluid holder in accordance with an embodiment of the present invention.
Figure 20:
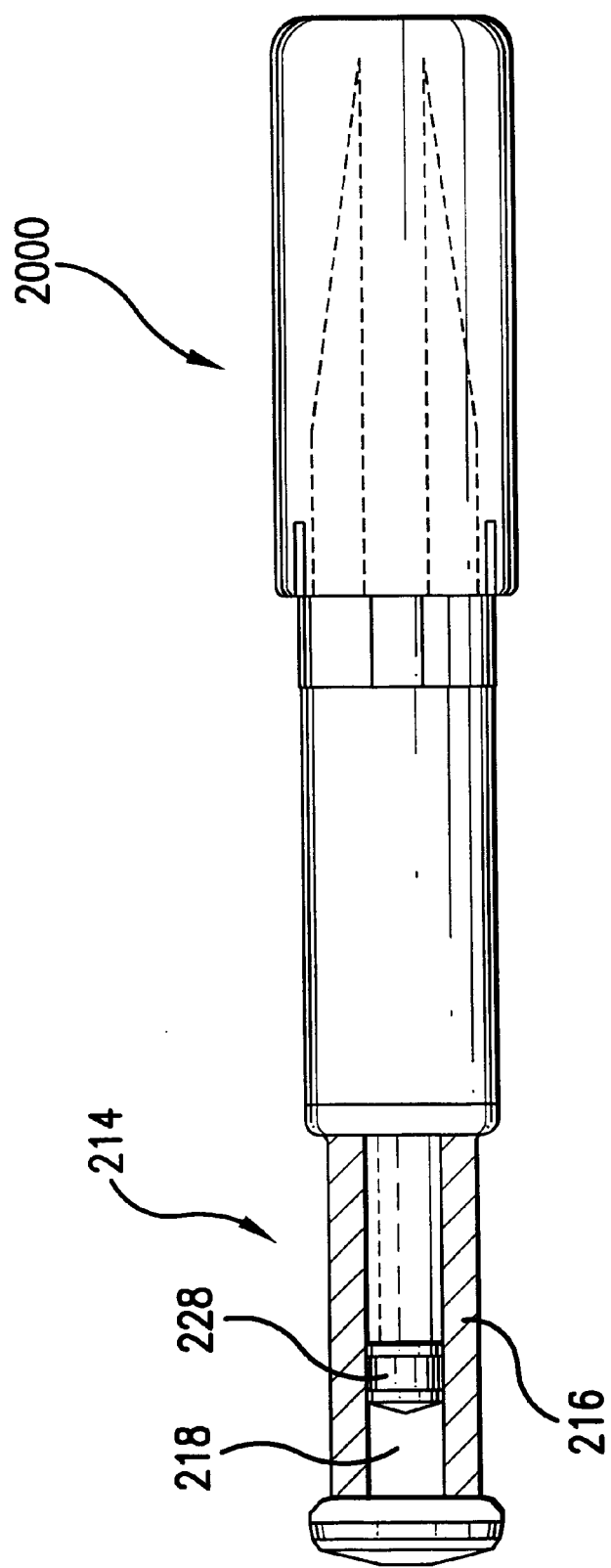
FIG. 20 is a side plan view of an ampule with a cap connected to a needle-less injector in accordance with an embodiment of the present invention.
Figure 21:
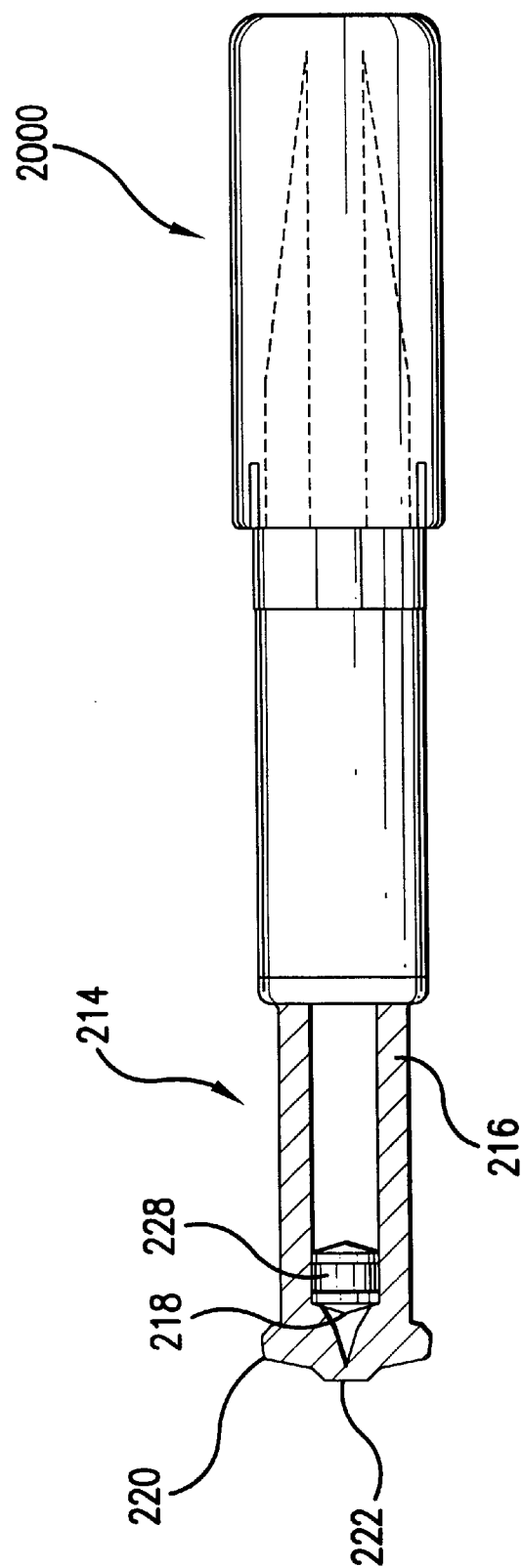
FIG. 21 is a side plan view of the ampule without the cap connected to a needle-less injector as shown in FIG. 20.
Figure 22:
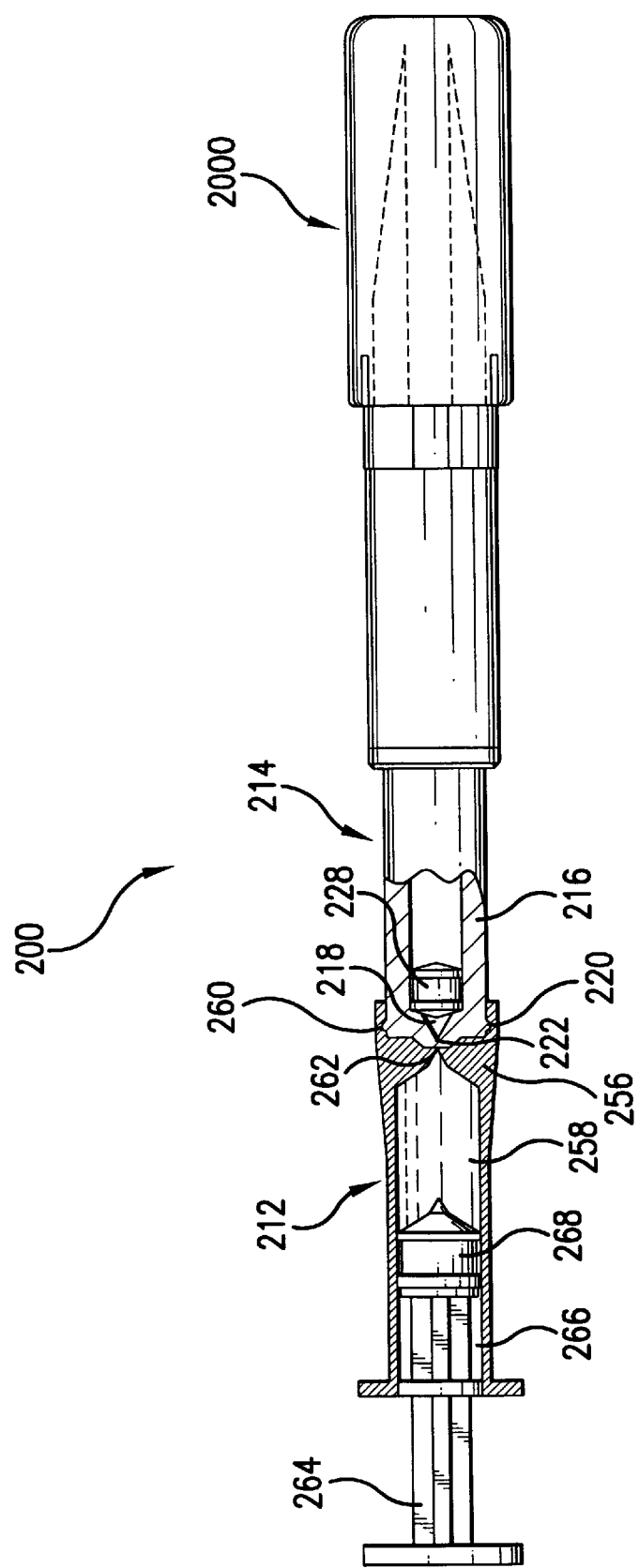
FIG. 22 is a side plan view of the ampule connected to the needle-less injector of FIGS. 20 and 21 combined with the cross-sectional view of the fluid holder shown in FIG. 19.
Figure 23:
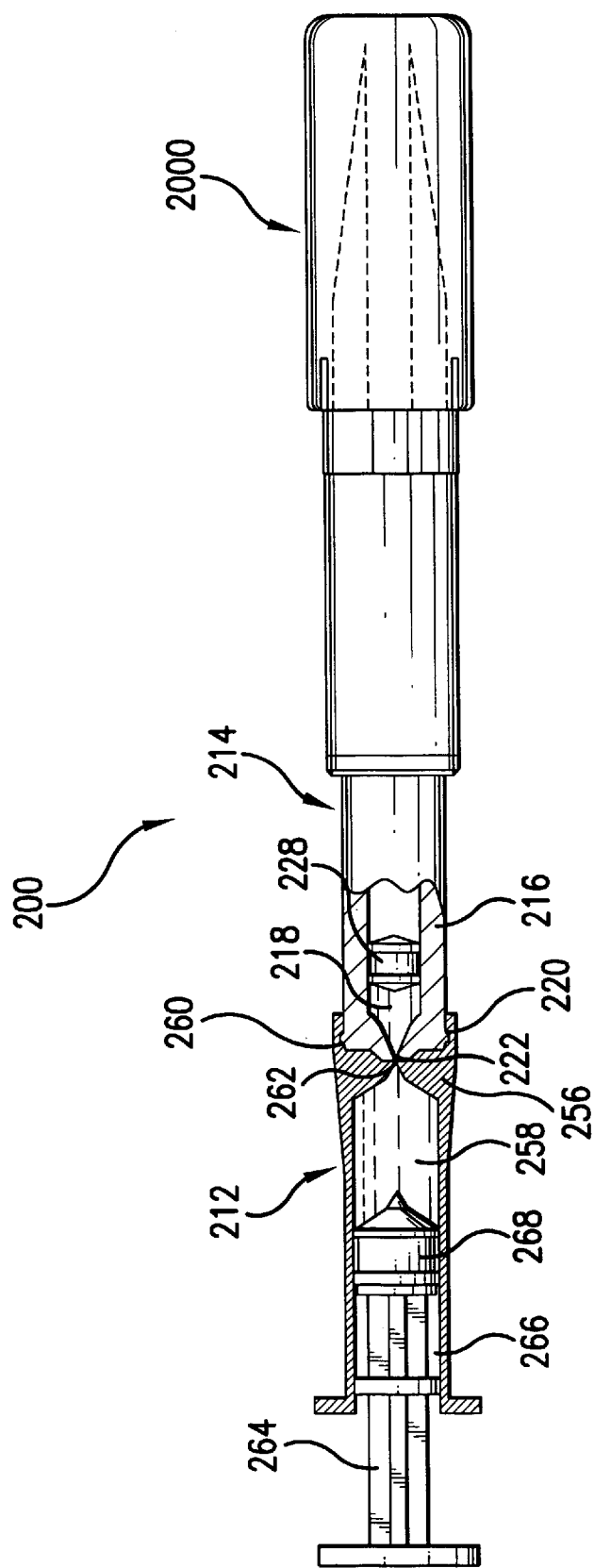
FIG. 23 is a cross-sectional view of the fluid holder and a side plan view of the ampule connected to the needle-less injector, shown in FIG. 19, as some fluid is transferred from the fluid holder to the ampule.
Figure 24:
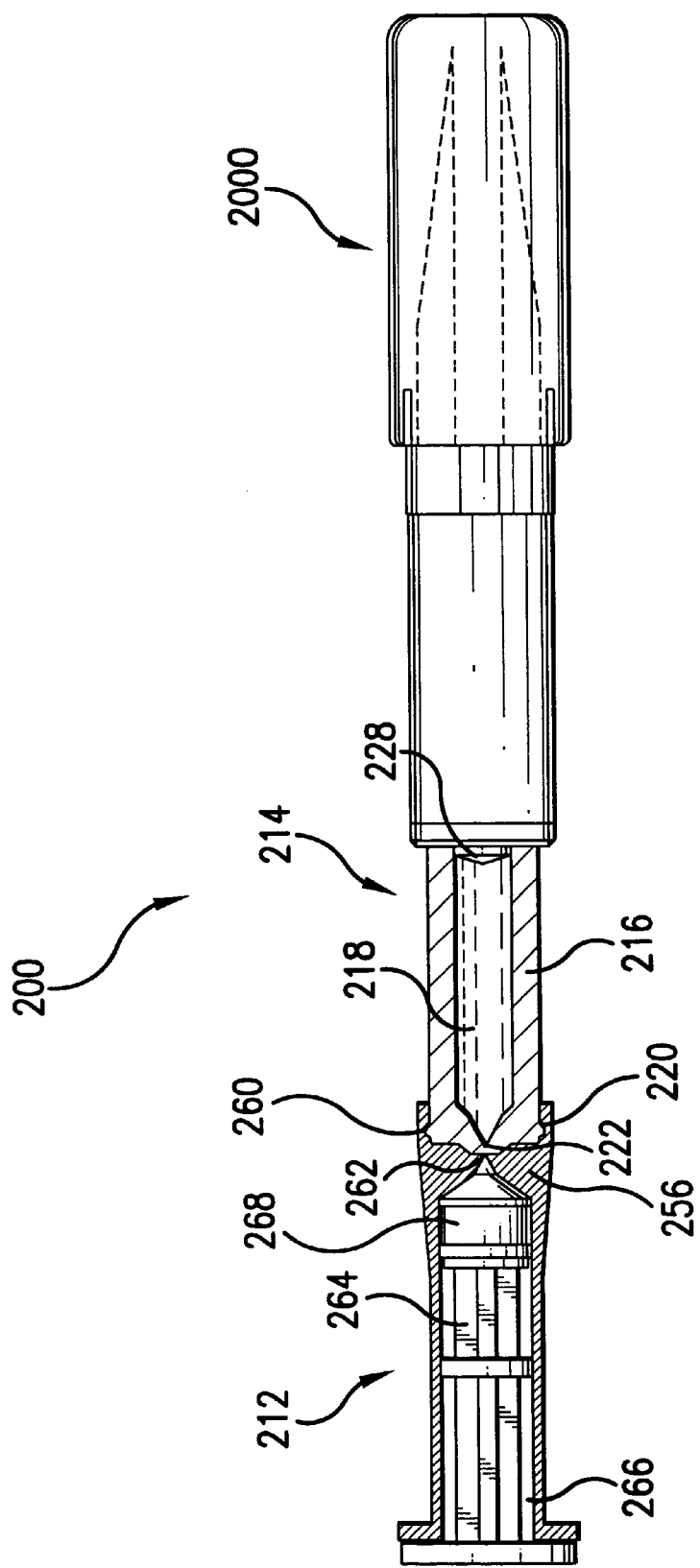
FIG. 24 is a cross-sectional view of the fluid holder and a side plan view of the ampule connected to the needle-less injector, shown in FIG. 19, after the fluid is transferred from the fluid holder to the ampule.

As shown in FIGS. 12–18, the reagent holder 114 stores the reagent and is configured for sterile docking (or coupling) with the diluent holder 112 containing the diluent. When the diluent holder 112 is docked with the reagent holder 114, the diluent plunger 164 and piston 168 are moved towards the opening 162 in the housing 156 to load the diluent in the reagent holder 114. In preferred embodiments, reagent holder 112 is the ampule for a needle-less injector or the like. As shown in FIG. 16, after loading the reagent holder 114 with diluent, the diluent plunger 164 is withdrawn a distance along the interior chamber 158 to remove any air bubble, and then the diluent holder 112 is removed and discarded. In alternative embodiments, after loading the reagent holder 114 (that is not connected to a needle-less injector 1000) with diluent, the reagent plunger and the bushing are used to remove any air or bubbles, and then the diluent holder 112 removed and discarded from the reagent holder 114, in a manner and structure similar to that described above in the first embodiment. The reagent holder 114, if an ampule that is separated from a needle-less injector 1000, is then threaded onto the body of a needle-less injector 1000.

In alternative embodiments, if the reagent holder 114 is not an ampule for a needle-less injector, the reagent holder 114, may be removed after receiving the diluent, and then coupled to an ampule for filling with the mixed medication. In further embodiments, the reagent holder 114 may be an ampule for a multi-use needle-less injector, syringe or the like.

FIGS. 19–26 illustrate a filling apparatus 200 in accordance with an embodiment of the present invention. The filling apparatus 200 includes a fluid holder 212. The filling apparatus 200 is similar to the apparatus 100 described above; however, the filing apparatus 200 does not mix a reagent in the ampule for a needle-less injector, syringe or the like. This removes one step of mixing a reagent and diluent to produce the medication.

An ampule 214 is sized to contain fluid or a medication prior to injection. In preferred embodiments, the ampule 214 is an ampule for use on a needle-less injector 2000 (see FIGS. 20–26). The ampule 214 includes a housing 216 that forms an interior chamber 218 for holding the fluid. One end of the housing 216 includes threads 220 and an orifice 222 for mating with corresponding threads and opening on the fluid holder 212 to provide fluid communication between the fluid holder 212 and the ampule 214. Another end of the housing 216 includes threads (not shown) and an opening 226 for mating with corresponding needle-less injector 2000. In alternative embodiments, the ends of the ampule 214 may be formed with other attachment structures, such as snaps, bars, friction fits or the like.

The ampule 214 also includes a piston 228 for maintaining the fluid in the interior chamber 218 and substantially prevent leakage out of the opening 266 of the housing 216. The piston 228 maintains the fluid in the interior chamber 218 so that it does not leak out of the orifice 222. As shown in FIGS. 20–26, the ampule 214 is attached to the needle-less injector 2000. In alternative embodiments, the ampule 214 is filled separately from the needle-less injector 2000 and includes an ampule plunger and a support bushing having an opening that allows passage of the ampule plunger rod through the support bushing to adjust the piston 228 after receipt of the fluid, in a manner and structure similar to that described in the first embodiment above.

The fluid holder 212 is sized to contain a fluid, such as a medication, a drug, a vaccine, or the like, for an injection with the ampule 214. The fluid holder 212 includes a housing 256 that forms an interior chamber 258 for holding the fluid. One end of the housing 256 includes threads 260 and an opening 262 for mating with corresponding threads 220 and orifice 222 on the ampule 214 to provide fluid communication between the fluid holder 212 and the ampule 214. In alternative embodiments, the end of the fluid holder 212 may be formed with other attachment structures, such as snaps, bars, friction fits or the like. Another end of the housing 256 includes a fluid plunger 264 and an opening 266 for receiving the fluid plunger 264.

The fluid holder 212 also includes a piston 268 coupled to the end of the fluid plunger 264 for maintaining the fluid in the interior chamber 258 and to substantially prevent leakage out of the opening 266 of the housing 256. The piston 268 maintains the fluid in the interior chamber 258 so that it does not leak out of the opening 262.

Figure 25:
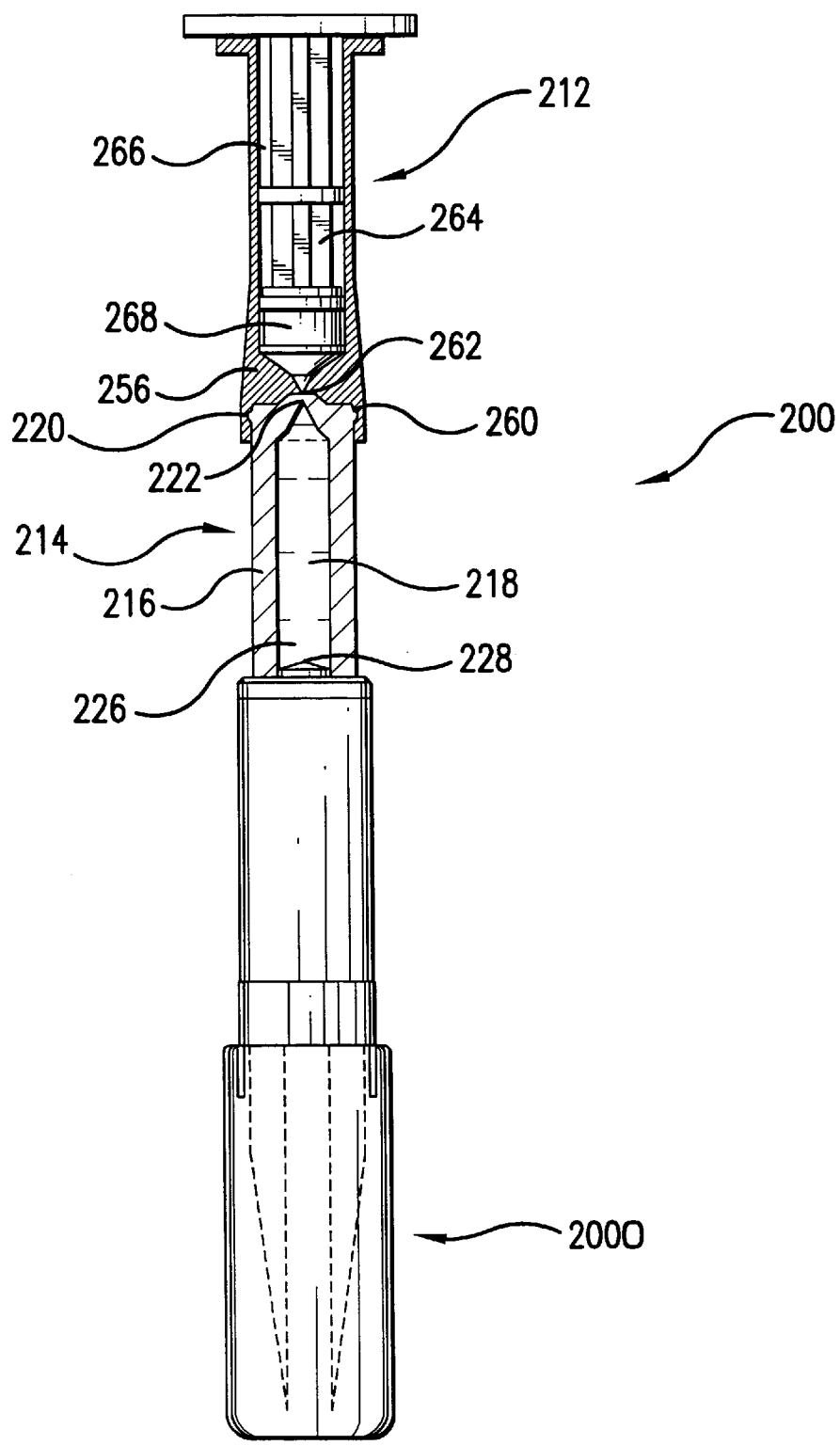
FIG. 25 is a cross-sectional view of the fluid holder and a side plan view of the ampule connected to the needle-less injector, shown in FIG. 19, turned to the vertical to draw out air bubbles as some is transferred back into the fluid holder from the ampule.
Figure 26:
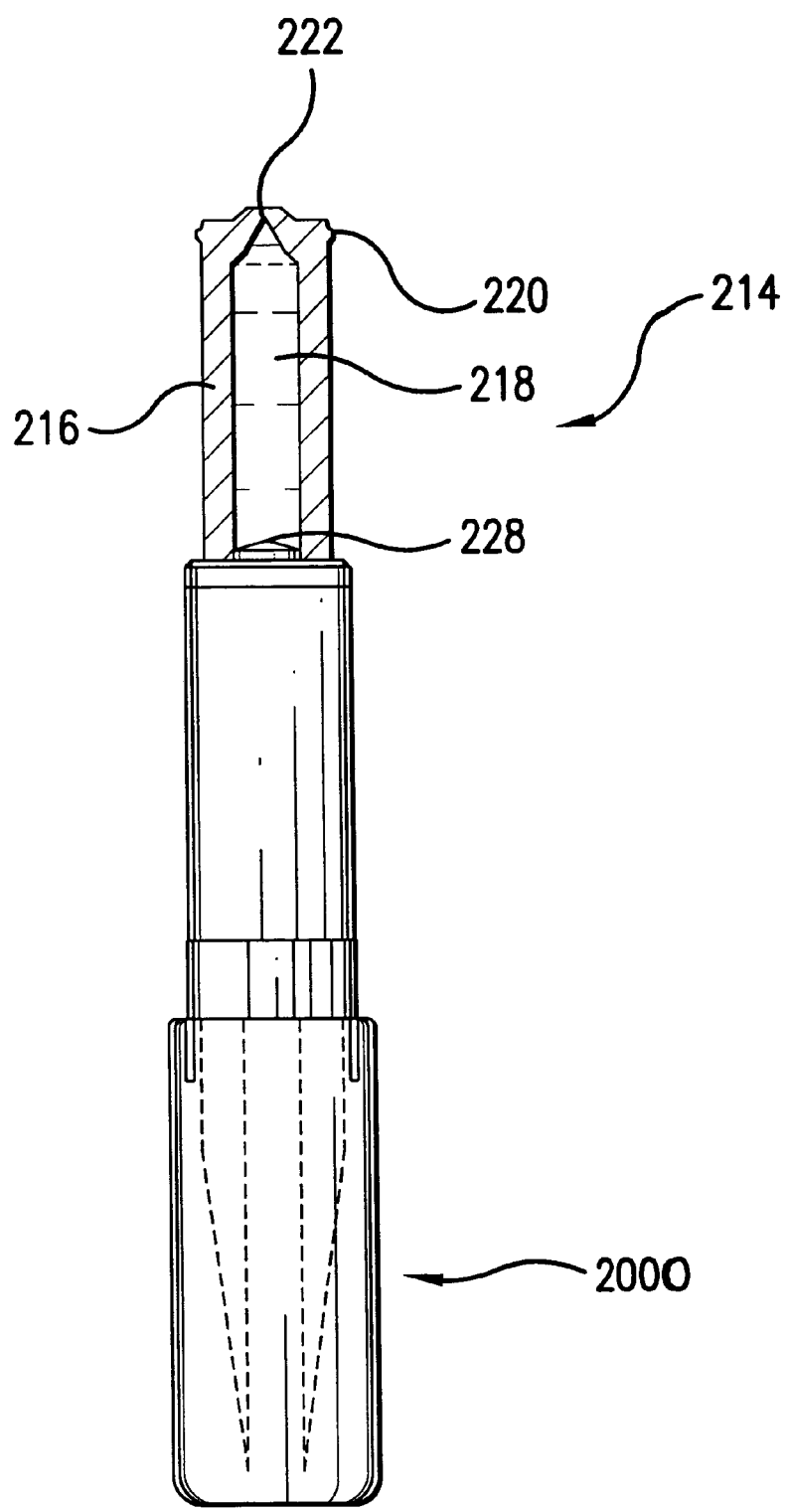
FIG. 26 is a side plan view of the ampule connected to the needle-less injector, shown in FIG. 19, after the fluid holder is removed from the ampule.

As shown in FIGS. 19—24, the ampule 214 is configured for sterile docking (or coupling) with the fluid holder 212 containing the fluid. When the fluid holder 212 is docked with the ampule 214, the fluid plunger 264 and piston 268 are moved towards the opening 262 in the housing 256 to load the fluid in the ampule 214. As shown in FIG. 25, after loading the ampule 214 with fluid, the fluid plunger 264 is withdrawn a distance along the interior chamber 258 to remove any air bubble, and then the fluid holder 212 is removed and discarded (see FIG. 26). In preferred embodiments, the ampule 214 is held vertically to cause bubbles to congregate near the orifice 222 of the ampule 214. In alternative embodiments, after loading the ampule 214 (that is not connected to a needle-less injector 2000) with fluid, the ampule plunger and the bushing are used to remove any air or bubbles, and then the fluid holder 212 removed and discarded from the ampule 214, in a manner and structure similar to that described above in the first embodiment. If the ampule 214 is separated from a needle-less injector 2000, it is then threaded onto the body of a needle-less injector 2000.

In alternative embodiments, if the ampule 214 is not an ampule for a needle-less injector, the ampule 214, may be removed after receiving the fluid, and then coupled to another ampule for filling. In further embodiments, the ampule 214 may be an ampule for a multi-use needle-less injector, syringe or the like.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In combination, an ampule adapted for use with a needle-less injector and an apparatus for filling an ampule of a needle-less injector suitable for injecting a fluid, the combination comprising:

the ampule; and a fluid holder containing the fluid, wherein the fluid holder has a fluid plunger rod, said rod having a longitudinal axis;

the ampule is matingly attached directly to the fluid holder to provide fluid communication between the ampule and the fluid holder; and the fluid plunger rod is configured to be slideably depressed in a rotation-free manner, upon application of pressure along the longitudinal axis of the fluid plunger rod, to load the fluid into the ampule of the needle-less injector.

2. The combination of claim 1, wherein the ampule is attached to the fluid holder by an attachment mechanism selected from the group consisting of mutual threads, snaps, and friction fits.

3. The combination of claim 2, wherein the ampule is attached to the fluid holder so as to provide direct, needle-less fluid communication between the ampule and the fluid holder.

4. The combination of claim 1, wherein the ampule has an ampule plunger rod, said rod being configured to be depressed to expel bubbles back into the fluid holder from the filled ampule.

5. The combination of claim 4, wherein the ampule is attached to the fluid holder by an attachment mechanism selected from the group consisting of mutual threads, snaps, and friction fits.

6. The combination of claim 1, wherein the fluid can be loaded into the ampule just prior to injection of the fluid due to a short shelf life of the fluid.

7. The combination of claim 1, wherein the ampule can be attached to the needle-less injector after filling the ampule with the fluid.

8. In combination, an ampule adapted for use with a needle-less injector and an apparatus for filling an ampule of a needle-less injector suitable for injecting a fluid, the combination comprising:

the ampule; and a fluid holder containing the fluid, wherein the fluid holder has a fluid plunger rod, said rod having a longitudinal axis;

the ampule is matingly attached directly to the fluid holder to provide fluid communication between the ampule and the fluid holder;

the ampule and fluid holder are made of rigid material; and the fluid plunger rod is configured to be slideably depressed in a rotation-free manner, upon application of pressure along the longitudinal axis of the fluid plunger rod, to load the fluid into the ampule of the needle-less injector.

9. In combination, an ampule adapted for use with a needle-less injector and an apparatus for filling an ampule of a needle-less injector suitable for injecting a fluid, the combination comprising:

the ampule, said ampule having an interior chamber; and a fluid holder, said holder having an interior chamber that contains the fluid, wherein the fluid holder has a fluid plunger rod, said rod having a longitudinal axis;

the ampule is matingly attached directly to the fluid holder so as to define a needle-less, unobstructed fluid-communication path between the interior chamber of the fluid holder and the interior chamber of the ampule upon attachment of the ampule to the fluid holder and prior to application of any pressure on said fluid plunger rod to move the fluid out of the fluid holder; and the fluid plunger rod is configured to be slideably depressed, upon application of pressure along the longitudinal axis of the fluid plunger rod, to load the fluid into the ampule of the needle-less injector.

10. The combination of claim 9, further including an ampule plunger rod, wherein said rod is configured to be depressed to expel bubbles back into the fluid holder from the filled ampule.

11. In combination, an ampule adapted for use with a needle-less injector and an apparatus for filling an ampule of a needle-less injector suitable for injecting a fluid, the combination comprising:

the ampule, said ampule having an interior chamber; and a fluid holder, said fluid holder having an interior chamber that contains the fluid, wherein the fluid holder has a fluid plunger rod, said rod having a longitudinal axis;

the ampule is matingly attached directly to the fluid holder so as to define a needle-less, unobstructed fluid-communication path between the interior chamber of the fluid holder and the interior chamber of the ampule upon attachment of the ampule to the fluid holder and prior to application of any pressure on said fluid plunger rod to move the fluid out of the fluid holder;

the ampule and fluid holder are made of rigid material and are matingly attached to each other by an attachment mechanism selected from the group consisting of mutual threads, snaps, and friction fits;

the fluid plunger rod is configured to be slideably depressed, upon application of pressure along the longitudinal axis of the fluid plunger rod, to load the fluid into the ampule of the needle-less injector; and the ampule has an ampule plunger rod, said rod being configured to be depressed to expel bubbles back into the fluid holder from the filled ampule.

12. A method of filling an ampule of a needle-less injector suitable for injecting fluid, the method comprising the steps of:

providing a fluid holder containing the fluid;

providing the fluid holder with a fluid plunger rod having a longitudinal axis;

adapting the fluid holder to be matingly attached directly to an ampule to provide fluid communication between the ampule and the fluid holder; and slideably depressing the fluid plunger rod in a rotation-free manner by applying pressure along the longitudinal axis thereof to load the fluid into an ampule.

13. The method of claim 12, further comprising the steps of:

providing an ampule;

providing an ampule plunger rod for the ampule; and after the fluid is loaded into the ampule, depressing the ampule plunger rod to expel bubbles into the fluid holder from the filled ampule.

14. The method of claim 12, wherein the step of attaching includes using an attachment mechanism selected from the group consisting of mutual threads, snaps, and friction fits.

15. The method of claim 13, wherein the ampule is filled with fluid just prior to injection of the fluid due to a short shelf life of the fluid.

16. The method of claim 13, further comprising the step of attaching the ampule to the needle-less injector after filling the ampule with the fluid.

17. A method of filling an ampule of a needle-less injector suitable for injecting fluid, the method comprising the steps of:

providing a fluid holder containing the fluid;

providing the fluid holder with a fluid plunger rod having a longitudinal axis;

adapting the fluid holder to be matingly attached directly to an ampule so as to define a needle-less, unobstructed fluid-communication path between the interior chamber of the fluid holder and the interior chamber of the ampule upon attachment of the ampule to the fluid holder and prior to application of any pressure on said fluid plunger rod to move the fluid out of the fluid holder; and slideably depressing the fluid plunger rod by applying pressure along the longitudinal axis thereof to load the fluid into an ampule.

18. The method of claim 17, further comprising the steps of:

providing an ampule;

providing the ampule with an ampule plunger rod; and depressing the ampule plunger rod to expel bubbles into the fluid holder from the filled ampule, wherein the ampule and the fluid holder are made of rigid material.

19. The method of claim 18, wherein the step of attaching includes using an attachment mechanism selected from the group consisting of mutual threads, snaps, and friction fits.

20. An apparatus for mixing medication and filling an ampule of a needle-less injector suitable for injecting liquid medication, the apparatus comprising:

a reagent holder containing a reagent; and a diluent holder containing a diluent, and having a diluent plunger rod, said diluent plunger rod having a longitudinal axis, wherein the reagent holder is matingly attached directly to the diluent holder to provide fluid communication between the reagent holder and the diluent holder, and wherein the diluent plunger rod is configured to be slideably depressed in a rotation-free manner, upon application of pressure along the longitudinal axis of the diluent plunger rod, to load the diluent into the reagent holder to mix with the reagent to produce the liquid medication for filling the ampule of the needle-less injector.

21. An apparatus in accordance with claim 20, wherein the reagent holder is the ampule of the needle-less injector.

22. An apparatus in accordance with claim 20, wherein the reagent holder further includes a reagent plunger rod, and wherein after the reagent and the diluent are mixed in the reagent holder to produce the liquid medication, the reagent plunger rod is depressed to load the liquid medication back into the diluent holder for filling the ampule of the needle-less injector.

23. An apparatus in accordance with claim 20, wherein the reagent and diluent are mixed just prior to injection of the liquid medication due to a short shelf life of the liquid medication.

24. An apparatus in accordance with claim 20, wherein the ampule of the needle-less injector is attached to the needle-less injector after filling with the liquid medication.

25. An apparatus for mixing medication and filling an ampule of a needle-less injector suitable for injecting liquid medication, the apparatus comprising:

a reagent holder containing a reagent; and a diluent holder containing a diluent, the diluent holder serving as the ampule of the needle-less injector, and having a diluent plunger rod, said diluent plunger rod having a longitudinal axis, wherein the reagent holder is matingly attached directly to the diluent holder to provide fluid communication between the reagent holder and the diluent holder, and wherein the diluent plunger rod is configured to be slideably depressed in a rotation-free manner, upon application of pressure along the longitudinal axis of the diluent plunger rod, to load the diluent into the reagent holder to mix with the reagent to produce the liquid medication for filling the ampule of the needle-less injector.

26. A reagent holder for mixing medication and filling an ampule of a needle-less injector suitable for injecting liquid medication, the reagent holder comprising:

a housing containing a reagent;

an attachment mechanism disposed on said housing; and a reagent plunger rod coupled to the housing to contain the reagent in the housing, said reagent plunger rod having a longitudinal axis, wherein when the reagent holder is matingly attached directly to the ampule of a needle-less injector by the attachment mechanism, fluid communication is provided between the reagent holder and the ampule, and wherein after a diluent is introduced into said housing to mix with the reagent and form a liquid medication, the liquid medication is expelled from the reagent holder when the reagent plunger rod is slideably depressed in a rotation-free manner, upon application of pressure along the longitudinal axis of the reagent plunger rod.

27. A reagent holder in accordance with claim 26, wherein after the reagent and the diluent are mixed in the reagent holder to produce the liquid medication, the reagent plunger rod is depressed to load the liquid medication into the ampule of the needle-less injector to fill the ampule of the needle-less injector.

28. An apparatus for mixing medication and filling an ampule of a needle-less injector suitable for injecting liquid medication, the apparatus comprising:

a reagent holder, said reagent holder having an interior chamber containing a reagent; and a diluent holder, said diluent holder having an interior chamber containing a diluent, and said diluent holder having a diluent plunger rod, and said diluent plunger rod having a longitudinal axis, wherein the reagent holder is matingly attached directly to the diluent holder so as to define a needle-less, unobstructed fluid-communication path between the interior chamber of the diluent holder and the interior chamber of the reagent holder upon attachment of the reagent holder to the diluent holder and prior to application of any pressure on said diluent plunger rod to move the diluent out of the diluent holder; and wherein the diluent plunger rod is configured to be slideably depressed, upon application of pressure along the longitudinal axis of the diluent plunger rod, to load the diluent into the reagent holder to mix with the reagent to produce the liquid medication for filling the ampule of the needle-less injector.

29. An apparatus in accordance with claim 28, wherein the reagent holder is the ampule of the needle-less injector.

30. An apparatus in accordance with claim 28, wherein the reagent holder further includes a reagent plunger rod, and wherein after the reagent and the diluent are mixed in the reagent holder to produce the liquid medication, the reagent plunger rod is depressed to load the liquid medication back into the diluent holder for filling the ampule of the needle-less injector.

31. An apparatus in accordance with claim 28, wherein the reagent and diluent are mixed just prior to injection of the liquid medication due to a short shelf life of the liquid medication.

32. An apparatus in accordance with claim 28, wherein the ampule of the needle-less injector is attached to the needle-less injector after filling with the liquid medication.

33. An apparatus for mixing medication and filling an ampule of a needle-less injector suitable for injecting liquid medication, the apparatus comprising:

a reagent holder, said reagent holder having an interior chamber containing a reagent; and a diluent holder, said diluent holder having an interior chamber containing a diluent, the diluent holder serving as the ampule of the needle-less injector, and having a diluent plunger rod, and said diluent plunger rod having a longitudinal axis, wherein the reagent holder is matingly attached directly to the diluent holder so as to define a needle-less, unobstructed fluid-communication path between the interior chamber of the diluent holder and the interior chamber of the reagent holder upon attachment of the reagent holder to the diluent holder and prior to application of any pressure on said diluent plunger rod to move the diluent out of the diluent holder, and wherein the diluent plunger rod is configured to be slideably depressed, upon application of pressure along the longitudinal axis of the diluent plunger rod, to load the diluent into the reagent holder to mix with the reagent to produce the liquid medication for filling the ampule of the needle-less injector.

34. A reagent holder for mixing medication and filling an ampule of a needle-less injector suitable for injecting liquid medication, the reagent holder comprising:

a housing, said housing having an interior chamber containing a reagent, and said housing including an attachment mechanism disposed on said housing; and a reagent plunger rod coupled to the housing to contain the reagent in the housing, said reagent plunger rod having a longitudinal axis, wherein when the reagent holder is matingly attached directly to the ampule of a needle-less injector by the attachment mechanism, a needle-less, unobstructed fluid-communication path is defined between the interior chamber of the housing and the interior chamber of the ampule upon attachment of the housing to the ampule; and wherein after a diluent is introduced into said housing to mix with the reagent and form a liquid medication, the liquid medication is expelled from the reagent holder when the reagent plunger rod is slideably depressed, upon application of pressure along the longitudinal axis of the reagent plunger rod.

35. A reagent holder in accordance with claim 34, wherein after the reagent and the diluent are mixed in the reagent holder to produce the liquid medication, the reagent plunger rod is depressed to load the liquid medication into the ampule of the needle-less injector to fill the ampule of the needle-less injector.

36. An apparatus for mixing medication and filling an ampule of a needle-less injector suitable for injecting liquid medication, the apparatus comprising:

a reagent holder, said reagent holder having an interior chamber containing a reagent; and a diluent holder, said diluent holder having an interior chamber containing a diluent, and said diluent holder having a diluent plunger rod, and said diluent plunger rod having a longitudinal axis, wherein the reagent holder is matingly attached directly to the diluent holder so as to define a needle-less, unobstructed fluid-communication path between the interior chamber of the diluent holder and the interior chamber of the reagent holder upon attachment of the reagent holder to the diluent holder and prior to application of any pressure on said diluent plunger rod to move the diluent out of the diluent holder; and wherein the diluent plunger rod is configured to be slideably depressed in a rotation-free manner, upon application of pressure along the longitudinal axis of the diluent plunger rod, to load the diluent into the reagent holder to mix with the reagent to produce the liquid medication for filling the ampule of the needle-less injector.

37. An apparatus in accordance with claim 36, wherein the reagent holder is the ampule of the needle-less injector.

38. An apparatus in accordance with claim 36, wherein the reagent holder further includes a reagent plunger rod, and wherein after the reagent and the diluent are mixed in the reagent holder to produce the liquid medication, the reagent plunger rod is depressed to load the liquid medication back into the diluent holder for filling the ampule of the needle-less injector.

39. An apparatus in accordance with claim 36, wherein the reagent and diluent are mixed just prior to injection of the liquid medication due to a short shelf life of the liquid medication.

40. An apparatus in accordance with claim 36, wherein the ampule of the needle-less injector is attached to the needle-less injector after filling with the liquid medication.

41. An apparatus for mixing medication and filling an ampule of a needle-less injector suitable for injecting liquid medication, the apparatus comprising:

a reagent holder, said reagent holder having an interior chamber containing a reagent; and a diluent holder, said diluent holder having an interior chamber containing a diluent, the diluent holder serving as the ampule of the needle-less injector, and having a diluent plunger rod, and said diluent plunger rod having a longitudinal axis, wherein the reagent holder is matingly attached directly to the diluent holder so as to define a needle-less, unobstructed fluid-communication path between the interior chamber of the diluent holder and the interior chamber of the reagent holder upon attachment of the reagent holder to the diluent holder and prior to application of any pressure on said diluent plunger rod to move the diluent out of the diluent holder, and wherein the diluent plunger rod is configured to be slideably depressed in a rotation-free manner, upon application of pressure along the longitudinal axis of the diluent plunger rod, to load the diluent into the reagent holder to mix with the reagent to produce the liquid medication for filling the ampule of the needle-less injector.

42. A reagent holder for mixing medication and filling an ampule of a needle-less injector suitable for injecting liquid medication, the reagent holder comprising:

a housing, said housing having an interior chamber containing a reagent, and said housing including an attachment mechanism disposed on said housing; and a reagent plunger rod coupled to the housing to contain the reagent in the housing, said reagent plunger rod having a longitudinal axis, wherein when the reagent holder is matingly attached directly to the ampule of a needle-less injector by the attachment mechanism, a needle-less, unobstructed fluid-communication path is defined between the interior chamber of the housing and the interior chamber of the ampule upon attachment of the housing to the ampule; and wherein after a diluent is introduced into said housing to mix with the reagent and form a liquid medication, the liquid medication is expelled from the reagent holder when the reagent plunger rod is slideably depressed in a rotation-free manner, upon application of pressure along the longitudinal axis of the reagent plunger rod.

43. A reagent holder in accordance with claim 42, wherein after the reagent and the diluent are mixed in the reagent holder to produce the liquid medication, the reagent plunger rod is depressed to load the liquid medication into the ampule of the needle-less injector to fill the ampule of the needle-less injector.

* * * * *